(12) United States Patent
Konishi et al.

(10) Patent No.: US 9,505,795 B2
(45) Date of Patent: Nov. 29, 2016

(54) METHOD FOR PRODUCING SCYLLO-INOSITOL

(71) Applicant: Asahi Kasei Chemicals Corporation, Tokyo (JP)

(72) Inventors: Kazunobu Konishi, Tokyo (JP); Shinichi Imazu, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 14/374,385

(22) PCT Filed: Jan. 22, 2013

(86) PCT No.: PCT/JP2013/051198
§ 371 (c)(1),
(2) Date: Jul. 24, 2014

(87) PCT Pub. No.: WO2013/115012
PCT Pub. Date: Aug. 8, 2013

(65) Prior Publication Data
US 2014/0370549 A1  Dec. 18, 2014

(30) Foreign Application Priority Data

Feb. 2, 2012 (JP) .................. 2012-020556
Nov. 12, 2012 (JP) .................. 2012-248490

(51) Int. Cl.
| | |
|---|---|
| *C07H 15/207* | (2006.01) |
| *C12N 9/16* | (2006.01) |
| *C12P 7/02* | (2006.01) |
| *C12P 19/46* | (2006.01) |
| *C12N 9/90* | (2006.01) |

(Continued)

(52) U.S. Cl.
CPC .......... *C07H 15/207* (2013.01); *C12N 9/0006* (2013.01); *C12N 9/16* (2013.01); *C12N 9/90* (2013.01); *C12P 7/02* (2013.01); *C12P 7/18* (2013.01); *C12P 19/46* (2013.01); *C12Y 101/01018* (2013.01); *C12Y 301/03025* (2013.01); *C12Y 505/01004* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 2006/0240534 A1 | 10/2006 | Yamaguchi et al. | |
| 2010/0261238 A1 | 10/2010 | Yamaguchi et al. | |
| 2011/0207188 A1* | 8/2011 | Yoshida .............. | C12N 9/0006 435/155 |

FOREIGN PATENT DOCUMENTS

| | | |
|---|---|---|
| CN | 1867676 A | 11/2006 |
| DE | 3405663 A1 | 8/1985 |
| EP | 1674578 A1 | 6/2006 |

(Continued)

OTHER PUBLICATIONS

Michell., Inositol derivatives: evolution and functions., Nature Reviews (2008), vol. 9, pp. 151-161.*

(Continued)

*Primary Examiner* — Alexander Kim
(74) *Attorney, Agent, or Firm* — Morgan, Lewis & Bockius LLP

(57) ABSTRACT

The disclosure provides a method of producing a scyllo-inositol or a new scyllo-inositol derivative in a one-step process, from ubiquitous and inexpensive raw materials. Also provided is a scyllo-inositol derivative bonded to saccharides such as glucose and similar.

5 Claims, 6 Drawing Sheets

Retention time (min)
a) Before reaction; b) After 3 hours of reaction; c) After 20 hours of reaction
1) Glucose; 2) Scyllo-inositol; 3) Scyllo-inositol derivative

(51) Int. Cl.
*C12P 7/18* (2006.01)
*C12N 9/04* (2006.01)

(56) References Cited

FOREIGN PATENT DOCUMENTS

| JP | 08-00258 A | | 1/1996 |
|---|---|---|---|
| JP | 08-38188 A | | 2/1996 |
| JP | 08-89262 A | | 4/1996 |
| JP | 09-117295 A | | 5/1997 |
| JP | 09-140388 A | | 6/1997 |
| JP | 09-220093 A | | 8/1997 |
| JP | 10-42860 A | | 2/1998 |
| JP | 10-42882 A | | 2/1998 |
| JP | 10-42883 A | | 2/1998 |
| JP | 10-271995 A | | 10/1998 |
| JP | 2000-041689 A | | 2/2000 |
| JP | 2003-102492 A | | 4/2003 |
| JP | 2003-160478 A | | 6/2003 |
| JP | WO 2010/050231 | * | 5/2010 |
| JP | 2010-187688 A | | 9/2010 |
| WO | 00/56911 A1 | | 9/2000 |
| WO | 2005/035774 A1 | | 4/2005 |
| WO | 2011/063304 A1 | | 5/2011 |

OTHER PUBLICATIONS

Yoshida et al., Organiszation and Transcription of the myo-Inositol Operon, iol, of Bacillus subtilis., Journal of Bacteriology (1997), vol. 179, pp. 4591-4598.*
Bacillus cereus EC 5.5.1.4 (last viewed on Jan. 14, 2016).*
Bacillus cereus EC 3.1.3.25 (last viewed on Jan. 14, 2016).*
Bacillus subtilis EC 1.1.1.18 (last viewed on Jan. 14, 2016).*
EC 1.1.1.370 (last viewed on Jan. 14, 2016).*
Majumder et al., 1l-myo-Inositol-1-phosphate synthase., Biochimica et Biophysica Acta (1997), vol. 1348, Issues 1-2, pp. 245-256.*
Structure of Ins3P (last viewed on Jan. 15, 2016).*
Keasling, Manufacturing Molecules Thourgh Metabolic Engineering., Science (2010), vol. 330, Issue 6009, pp. 1355-1358).*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Partial Supplementary European Search Report issued in counterpart European Patent Application No. 13743267.0 dated Jan. 29, 2015.
Office Action dated May 8, 2015 ssued in counterpart Taiwanese Patent Application No. 102103677.
Yamaoka et al., "A cell factory of Bacillus subtilis engineered for the simple bioconversion of myo-inositol to scyllo-inositol, a potential therapeutic agent for Alzheimer's disease," Microbial Cell Factories, 10: 69 (2011).
Chen et al., "Cloning and Expression of the Inositol Monophosphatase Gene from Methanococcus jannaschii and Characterization of the Enzyme," Applied and Environmental Microbiology, 64: 2609-2615 (1998).
Kamano et al., "Isolation and Structure of Two New Glucosides, 1-O-β-D-Glucopyranosyl-scyllo-inositol and 1-O-β-D-Glucopyranosyl-proto-quercitol," Chem. Pharm. Bull., 19: 1113-1117 (1971).
McLaurin et al., "Inositol Stereoisomers Stabilize an Oligomeric Aggregate of Alzheimer Amyloid β Peptide and Inhibit Aβ-induced Toxicity," The Journal of Biological Chemistry, 275: 18495-18502 (2000).
Kamano et al., "Studies on the Constituents of Quercus supp. III. On the Constituents of *Quercus stenophylla* MAKINO," Yakugaku Zasshi, 89: 1302-1305 (1969).
Kohne et al., "Notiz zur Darstellung von scyllo-Inosit," Liebigs Ann. Chem., 866-868 (1985).
International Search Report issued in corresponding International Patent Application No. PCT/JP2013/051198 dated Apr. 23, 2014.
Office Action issued in counterpart Taiwanese Patent Application No. 102103677 dated Sep. 15, 2014.

* cited by examiner

FIG. 1 atgacagaag ataatattgc tccaatcacc tccgttaaag tagttaccga caagtgcacg
tacaaggaca acgagctgct caccaagtac agctacgaaa atgctgtagt tacgaagaca
gctagtggcc gcttcgatgt cacgcccact gttcaagact acgtgttcaa acttgactta
aaaaagccgg aaaaactagg aattatgctc attgggttag gtggcaacaa tggctccacc
ttagtggcct cggtattggc gaataagcac aatgtggagt ttcaaactaa ggaaggcgtt
aagcaaccaa actacttcgg ctccatgact caatgttcta ccttgaaact gggtgtcgat
gcggagggga atgacgttta tgctcctttt aactctctgt tgcccatggt tagcccaaac
gactttgtcg tctctggttg ggacatcaat aacgcagatc tatacgaagc tatgcagaga
agtcaggttc tcgaatatga tctgcaacaa cgcttgaagg cgaagatgtc cttggtgaag
cctcttcctt ccatttacta ccctgatttc attgcagcta atcaagatga gagagccaat
aactgcatca atttggatga aaaaggcaac gtaaccacga ggggtaagtg ggcccatctg
caacgcatca gacgcgatat tcagaatttc aaagaagaaa acgcccttga taaagtaatc
gttctttgga ctgcaaatac tgagaggtac gtagaagtat ctcctggtgt taatgacacc
atggaaaacc tcttgcagtc tattaagaat gaccatgaag agattgctcc ttccacgatc
tttgcagcag catctatctt ggaaggtgtc ccctatatta atggttcacc gcagaatact
tttgttcccg gcttggttca gctggctgag catgagggta cattcattgc gggagacgat
ctcaagtcgg gacaaaccaa gttgaagtct gttctggccc agttcttagt ggatgcaggt
attaaaccgg tctccattgc atcctataac catttaggca ataatgacgg ttataactta
tctgctccaa aacaatttag gtctaaggag atttccaaaa gttctgtcat agatgacatc
atcgcgtcta atgatatctt gtacaatgat aaactgggta aaaaagttga ccactgcatt
gtcattaaat atatgaagcc cgtcggggac tcaaaagtgg caatggacga gtattacagt
gagttgatgt taggtggcca taaccggatt tccattcaca atgtttgcga agattcttta
ctggctacgc ccttgatcat cgatctttta gtcatgactg agttttgtac aagagtgtcc
tataagaagg tggacccagt taaagaagat gctggcaaat ttgagaactt ttatccagtt
ttaaccttct tgagttactg gttaaaagct ccattaacaa gaccaggatt tcacccggtg
aatggcttaa acaagcaaag aaccgcctta gaaaattttt taagattgtt gattggattg
ccttctcaaa acgaactaag attcgaagag agattgttgt aa (SEQ ID NO 1)

FIG. 2 atgcatccgatgctgaacatcgccgtgcgcgcagcgcgcaaggcgggtaatttaattgcc
aaaaactatgaaaccccggacgctgtagaagcgagccagaaaggcagtaacgatttcgtg
accaacgtagataaagctgccgaagcggtgattatcgacacgattcgtaaatcttaccca
cagcacaccatcatcaccgaagaaagcggtgaacttgaaggtactgatcaggatgttcaa
tgggttatcgatccactggatggcactaccaactttatcaaacgtctgccgcacttcgcg
gtatctatcgctgttcgtatcaaaggccgcaccgaagttgctgtggtatacgatcctatg
cgtaacgaactgttcaccgccactcgcggtcagggcgcacagctgaacggctaccgactg
cgcggcagcaccgctcgcgatctcgacggtactattctggcgaccggcttcccgttcaaa
gcaaaacagtacgccactacctacatcaacatcgtcggcaaactgttcaacgaatgtgca
gacttccgtcgtaccggttctgcggcgctggatctggcttacgtcgctgcgggtcgtgtt
gacggtttctttgaaatcggtctgcgcccgtgggacttcgccgcaggcgagctgctggtt
cgtgaagcgggcggcatcgtcagcgacttcaccggtggtcataactacatgctgaccggt
aacatcgttgctggtaacccgcgcgttgttaaagccatgctggcgaacatgcgtgacgag
ttaagcgacgctctgaagcgttaa (SEQ ID NO 3)

FIG. 3

```
         10         20         30         40         50         60
 atgagtttac gtattggcgt aattggaact ggagcaatcg gaaaagaaca tattaaccgt 70         80         90        100        110        120
 atcacgaaca agctgtcagg cgcggaaatt gtagctgtaa cggatgttaa tcaagaagct 130        140        150        160        170        180
 gcacaaaagg tcgttgagca ataccaatta aacgcgacgg tttatccgaa tgatgacagc 190        200        210        220        230        240
 ttgcttgcag acgaaaatgt agacgctgtt ttagtgacaa gctgggggcc tgcgcatgag 250        260        270        280        290        300
 tcaagcgtgc tgaaagcgat taaagcccag aaatatgtgt tctgtgaaaa accgctcgcg 310        320        330        340        350        360
 acaacggctg aaggatgcat gcgcattgtc gaagaagaaa tcaaagtggg caaacgcctt 370        380        390        400        410        420
 gttcaagtcg gcttcatgcg ccgttatgac agcggttacg tacagctgaa agaagcgctc 430        440        450        460        470        480
 gataatcatg tcatcggcga gcctcttatg attcactgcg cgcaccgcaa cccgactgta 490        500        510        520        530        540
 ggagataact atacaacgga tatggctgta gtcgacacgc ttgttcatga aattgacgtg 550        560        570        580        590        600
 ctccactggc tcgtcaatga tgactacgag tccgttcaag tcatctatcc gaaaaaatca 610        620        630        640        650        660
 aaaaacgcgc ttccacattt aaaagatccg caaatcgtcg tgattgaaac aaaaggcggt 670        680        690        700        710        720
 atcgtcatca atgctgaaat ctatgtgaac tgtaaatacg gctatgacat tcaatgtgaa 730        740        750        760        770        780
 atcgtcggag aagacggcat catcaagctt cccgagccat caagcatcag cttgagaaaa 790        800        810        820        830        840
 gaaggcagat tcagcactga tattttgatg gattggcaga gacgctttgt cgctgcgtat 850        860        870        880        890        900
 gatgtggaaa tccaagactt tattgattcg attcaaaaga aaggcgaggt cagcggaccg 910        920        930        940        950        960
 acggcatggg acggctatat tgctgctgtc acgactgacg cgtgtgtaaa agcccaggaa 970        980        990       1000       1010       1020
 tctggacaaa aagaaaaggt tgaattgaag gaaaaaccgg aattctatca atcttttaca 1030       1040
 acagttcaaa actaa        (SEQ ID NO 5)
```

Fig. 4

```
            10         20         30         40         50         60
     atgataacgc ttttaaaggg gagaagaaaa gtggatacga tcaaggttgg aatattagga 70         80         90        100        110        120
     tacggattgt ccggttctgt ttttcacggg ccgctgctgg atgttctgga tgaatatcaa 130        140        150        160        170        180
     atcagcaaaa tcatgacatc acggacagaa gaagtgaaac gggatttcc agatgctgag 190        200        210        220        230        240
     gttgtacatg agcttgaaga aatcacaaat gaccctgcca ttgagcttgt cattgtcacc 250        260        270        280        290        300
     accccgagcg gccttcatta cgagcatact atggcatgca tacaggccgg aaaacatgtt 310        320        330        340        350        360
     gtgatggaaa aaccaatgac agcaacggcc gaagaggggg aaacattaaa aagggctgcc 370        380        390        400        410        420
     gatgaaaaag gcgtattatt aagcgtatat cataaccgac gctgggataa cgattttta 430        440        450        460        470        480
     acgattaaaa agctgatctc tgagggatcc cttgaagata tcaatacata tcaagtttcc 490        500        510        520        530        540
     tataaccgct acagacctga agttcaagcg cggtggcggg aaaaagaagg cactgccact 550        560        570        580        590        600
     ggtacgctgt atgatctcgg ctcccacatc atagaccaaa ccctgcattt gtttgggatg 610        620        630        640        650        660
     cctaaagccg tgactgcaaa cgtgatggcc cagcgggaaa atgccgaaac ggttgactat 670        680        690        700        710        720
     tttcatttaa ccctggatta tggcaagctt caagccattc tatacggagg atcaatcgtt 730        740        750        760        770        780
     ccggcaaacg gacctcgtta tcaaatccat ggaaaagatt ctagctttat caaatatgga 790        800        810        820        830        840
     attgacggac aggaagacgc actcagagcg ggaagaaaac cagaggatga cagctggggt 850        860        870        880        890        900
     gcggatgttc cggagtttta cggaaagctt acaaccattc gtggctccga caaaaaaaca 910        920        930        940        950        960
     gaaacgattc catcagtaaa tggctcctac cttacttatt accgtaaaat agcggaaagc 970        980        990       1000       1010       1020
     atacgagaag gtgctgcgct gccagtcact gctgaggaag gtattaatgt catccgcatc 1030       1040       1050       1060       1070       1080
     attgaagccg cgatggaaag cagtaaagag aaacgaacca ttatgctgga gcactaa
     (SEQ ID NO 7)
```

Retention time (min)
a) Before reaction; b) After 3 hours of reaction; c) After 20 hours of reaction
1) Glucose; 2) Scyllo-inositol; 3) Scyllo-inositol derivative

METHOD FOR PRODUCING SCYLLO-INOSITOL

A computer readable text file, entitled "SequenceListing.txt," created on or about Jul. 24, 2014 with a file size of about 37 kb contains the sequence listing for this application and is hereby incorporated by reference in its entirety.

TECHNICAL FIELD

The present invention relates to the application of gene recombination technology in the production of scyllo-inositol. In particular, it relates to transformants capable of producing scyllo-inositol from ubiquitous raw materials such as glucose and the like by a one-step process and to a method for the industrial production of scyllo-inositol that utilizes these transformants. The invention also relates to a scyllo-inositol derivative that can be produced by the transformants, a method for its production, and a method for producing scyllo-inositol from the derivative.

BACKGROUND ART

Scyllo-inositol (cis-1,3,5-trans-2,4,6-cyclohexanehexyl) is an optically inactive isomer of inositol and is a compound that was found long ago in plants and animals. Recently, however, various bioactivities of scyllo-inositol have drawn attention.

For example, Non-patent Reference 1 reports that scyllo-inositol has an inhibitory effect on amyloid β protein aggregation. This effect suggests the potential usefulness of scyllo-inositol in the treatment of Alzheimer's disease. Patent Reference 1 claims a blood sugar-lowering agent containing scyllo-inositol as an active ingredient. Therefore, there clearly exists a need to industrially produce scyllo-inositol.

Classic production methods were extraction of scyllo-inositol from plants or chemical synthesis of this compound using myo-inositol as a raw material (Non-patent References 2 and 3, Patent Reference 2, and the like). In recent years, however, more efficient methods of producing scyllo-inositol using natural microorganisms or enzymes from microorganism have been studied.

Patent Reference 3 discloses a method for producing inositol stereoisomers in culture broth by culturing microorganisms belonging to the genus *Agrobacterium* in medium containing myo-inositol or producing inositol stereoisomers by causing cells or treated cells of microorganisms belonging to the genus *Agrobacterium* to act on myo-inositol. These isomerizations are said to convert myo-inositol into a mixture of scyllo-inositol, chiro-inositol (as a mixture of D- and L-forms), and neo-inositol.

Patent Reference 4 states that myo-inositol is converted into scyllo-inosose by causing *Pseudomonas* sp. AB10064 (FERM P-18330) or *Acetobacter* sp. AB10253 (FERM P-18868) to act on myo-inositol. Synthesis of scyllo-inositol by reducing the scyllo-inosose produced in this way by sodium borohydride was also attempted, but this reduction treatment basically produced scyllo-inositol only as a mixture with myo-inositol (that is, a retrograde reaction to the raw material). Therefore, it was necessary to increase the content of scyllo-inositol gradually while repeating conversion of myo-inositol into scyllo-inositol by microorganisms and reduction treatment by sodium borohydride in the method for producing scyllo-inositol described in Patent Reference 4.

Patent Reference 5 discloses a method for producing scyllo-inositol using myo-inositol as a raw material, in which myo-inositol is enzymatically converted into scyllo-inositol in a solution obtained by mixing myo-inositol 2-dehydrogenase (EC 1.1.1.18) which produces scyllo-inosose from myo-inositol, scyllo-inositol dehydrogenase which stereoselectively reduces scyllo-inosose to scyllo-inositol, and $NAD^+$ or $NADP^+$. The conversion of myo-inositol into scyllo-inositol is said to be 31% on a yield base in this reference.

Therefore, all of the above references relate to methods for producing scyllo-inositol using myo-inositol as a raw material; none teach the de novo biosynthesis of scyllo-inositol, that is, direct production of scyllo-inositol from ubiquitous raw materials such as glucose and the like by a one-step process.

In particular, myo-inositol itself is in the first place an extremely useful and valuable bioactive substance. Specifically, myo-inositol is widely utilized as a component of nutritional foods, feeds, pharmaceuticals, and the like since it is an essential substance for many higher animals. For example, myo-inositol is known to play an important role in the metabolism of fats and cholesterols and is held to be effective in the prevention and treatment of hypercholesterolemia and the like.

Therefore, many improvements are in fact being proposed for industrial-scale myo-inositol production processes. For example, Patent Reference 6 discloses the discovery and utilization of yeast of the genus *Candida* capable of secreting inositol extracellularly. Patent References 7 and 8 disclose the introduction of mutations to impart resistance to glucose antimetabolites and antibiotics, respectively, to the above yeast of the genus *Candida*. Patent References 9, 10, and 11 also disclose improvement of the yield of inositol by introducing mutations to impart resistance to tertiary amines, hexachlorocyclohexane, and cetyl trimethylammonium salt, respectively, to yeasts of the genus *Candida* having the ability to produce inositol. Patent Reference 12 discloses the introduction of a mutation to impart resistance to 6-halogeno-6-deoxyglucose to a yeast of the genus *Candida* having the ability to produce inositol. Patent Reference 13 also discloses the introduction of a mutation to impart resistance to halogenated pyruvic acid to a yeast of the genus *Candida* having the ability to produce inositol. In addition, Patent Reference 14 discloses that it is possible to impart the ability to produce inositol to a yeast of the genus *Candida* that does not have the ability to secrete inositol by transforming the yeast by inositol-1-phosphoric acid synthase-encoding DNA alone, based on the reasonable inference that inositol-1-phosphoric acid synthase is responsible for a rate-limiting reaction in the series of myo-inositol biosynthetic reactions. Patent Reference 15 discloses that the inositol productivity of the yeast is improved by introducing inositol-1-phosphoric acid synthase-encoding DNA alone into yeast under the control of a glycerol-3-phosphate dehydrogenase gene promoter.

All of the above tells us that establishing an efficient, economical production method for myo-inositol itself still remains a significant technical problem even today. Therefore, the scyllo-inositol production processes of the prior art that must use valuable, expensive myo-inositol as a raw material are obviously inefficient and uneconomical.

Moreover, none of the above references disclose or even suggest a scyllo-inositol derivative, especially scyllo-inositol derivatized from sugars.

PRIOR ART REFERENCES

Patent References

Patent Reference 1: JP Kokai 2003-160478
Patent Reference 2: West German Patent No. 3,405,663
Patent Reference 3: JP Kokai 9-140388
Patent Reference 4: JP Kokai 2003-102492
Patent Reference 5: JP Kokai 2010-187688
Patent Reference 6: JP Kokai 8-00258
Patent Reference 7: JP Kokai 8-38188
Patent Reference 8: JP Kokai 8-89262
Patent Reference 9: JP Kokai 9-117295
Patent Reference 10: JP Kokai 10-42860
Patent Reference 11: JP Kokai 10-42882
Patent Reference 12: JP Kokai 10-42883
Patent Reference 13: JP Kokai 2000-41689
Patent Reference 14: JP Kokai 9-220093
Patent Reference 15: JP Kokai 10-271995

Non-Patent References

Non-patent Reference 1: The Journal of Biological Chemistry, Vol. 275, No. 24, pp. 18495-18502 (2000)
Non-patent Reference 2: Yakugaku Zasshi, Vol. 89, pp. 1302-1305 (1969)
Non-patent Reference 3: Liebigs Ann. Chem., pp. 866-868 (1985)

SUMMARY OF THE INVENTION

Problems to be Solved by the Invention

Therefore, the first object of the present invention relates to an industrial production method capable of producing scyllo-inositol by a one-step process from inexpensive, ubiquitous raw materials such as glucose and the like. The present inventors also discovered the sugar-coupled scyllo-inositol derivative of the present invention for the first time during the course of this research. This scyllo-inositol derivative demonstrated remarkably superior water solubility even in comparison to the inherent water-solubility of scyllo-inositol. The finding of the present invention was surprising given that cellobiose (D-glucopyranosyl-(β1→4)-D-glucose) presents lower solubility than glucose. Therefore, the second object of the present invention is to provide a novel scyllo-inositol derivative.

Means Used to Solve the Above-Mentioned Problems

As was mentioned above, all of the recent research has concerned only the methods of enzymatic conversion of scyllo-inositol using myo-inositol as a raw material. None of the prior art references succeeded in constructing a functional de novo scyllo-inositol biosynthetic system inside a host microbial cell, that is, in establishing a method for the direct fermentative production of scyllo-inositol from ubiquitous raw materials such as glucose and the like by a one-step process.

However, the present inventors discovered that transformants expressing an inositol-1-phosphoric acid synthase gene, inositol monophosphatase gene, myo-inositol dehydrogenase gene, and scyllo-inositol dehydrogenase gene are capable of fermentatively producing scyllo-inositol from glucose directly in one step. The present inventors also discovered a novel scyllo-inositol derivative in cultures of such transformants.

Therefore, the first aspect of the present invention is:
(1) a method for producing scyllo-inositol and a scyllo-inositol derivative including the following steps:
  1) a step for preparing a transformed microorganism possessing an inositol-1-phosphoric acid synthase gene, inositol monophosphatase gene, myo-inositol dehydrogenase gene, and scyllo-inositol dehydrogenase gene; and
  2) a step for bringing the microorganism into contact with glucose or disaccharides or polysaccharides having glucose units under conditions suited to the growth and/or maintenance of the microorganism.

More specifically, it is a method for producing scyllo-inositol and a derivative thereof using a transformant wherein the transformant expresses an inositol-1-phosphoric acid synthase gene, inositol monophosphatase gene, myo-inositol dehydrogenase gene, and scyllo-inositol dehydrogenase gene.

The scyllo-inositol derivative produced in the culture of (1) above is a novel compound; glucose and scyllo-inositol are β1→4 bonded in this derivative. Therefore, one embodiment of the present invention is the production method according to (1) wherein the scyllo-inositol derivative is a compound shown by the following structural formula:

[Chemical Formula 1]

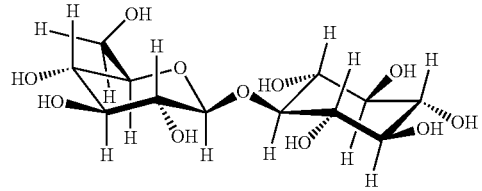

Surprisingly enough, enhancing the inositol monophosphatase activity of such transformants greatly improved the scyllo-inositol production capacity. Unexpectedly, scyllo-inositol was produced predominantly and production of myo-inositol was slight in these transformants. None of the prior literature of before the priority date of the present application either suggested or disclosed enhancing inositol monophosphatase activity for this purpose. Therefore, the second aspect of the present invention is:
(3) The production method according to (1) or (2) above wherein the transformed microorganism has a gene recombination or mutation to induce functional inositol monophosphatase overproduction or inositol monophosphatase activation.

Prokaryotic microorganisms typified by *Escherichia coli* are very attractive from the viewpoint of industrial fermentative production due to their rapid growth ability and ease of fermentation control and have advantages from the viewpoint of the practical accomplishment in the application of gene recombination techniques and the established safety. The many prokaryotic microorganisms that do not have a biosynthetic pathway for scyllo-inositol from glucose via myo-inositol also have an advantage in ease of control of scyllo-inositol productivity by the use of synthetic biology techniques in cooperation with genetic recombination techniques. Prokaryotic microbial hosts such as *E. coli* in particular make the application of synthetic biology techniques even easier since they do not have the ability to assimilate (ability to decompose) myo-inositol, an intermediate of the scyllo-inositol biosynthetic pathway.

Therefore, preferred embodiments of the present invention are:

(4) The production method according to any of (1) to (3) above wherein the transformed microorganism is derived from a microorganism that does not have the ability to assimilate myo-inositol; and (5) The production method according to any of (1) to (4) above wherein the transformed microorganism is derived from a bacterium selected from the group consisting of *Escherichia coli*, bacteria belonging to the genus *Bacillus*, bacteria belonging to the genus *Corynebacterium*, and bacteria belonging to the genus *Zymomonas*.

As regards preferred embodiment (3) above, regardless of whether or not the host microorganism has endogenous inositol monophosphatase activity, inducing overproduction of inositol monophosphatase within the cell can enhance the inositol monophosphatase activity of the cell. Inositol monophosphatase overproduction can be induced in the cell by applying various known techniques. Therefore, the present invention includes the following embodiments:

(6) The production method according to any of (3) to (5) above wherein the inositol monophosphatase overproduction is induced by, in the transformed microorganism:

a) introducing an exogenous inositol monophosphatase gene, b) increasing the number of copies of an endogenous inositol monophosphatase gene, c) introducing a mutation into a regulatory region of the endogenous inositol monophosphatase gene, d) replacing the regulatory region of the endogenous inositol monophosphatase gene with a high expression-inducing exogenous regulatory region, or e) deleting the regulatory region of the endogenous inositol monophosphatase gene; and (7) The production method according to (6) above wherein the inositol monophosphatase overexpression is induced by introducing an exogenous inositol monophosphatase gene into the above transformed microorganism.

In addition, when the host cell has an endogenous inositol monophosphatase gene, the inositol monophosphatase activity of the cell can be enhanced by the following embodiments as well. Therefore, the present invention also includes the following embodiment:

(8) The production method according to any of (3) to (5) above wherein the inositol monophosphatase activation is induced by, in the transformed microorganism:

f) introducing a mutation into an endogenous inositol monophosphatase gene, g) replacing all or part of the endogenous inositol monophosphatase gene, h) deleting part of the endogenous inositol monophosphatase gene, i) reducing other proteins that lower inositol monophosphatase activity, or j) reducing production of compounds that lower inositol monophosphatase activity.

The present invention also intends transformants for use in the production method of scyllo-inositol and a derivative thereof. Therefore, another aspect of the present invention is:

(9) a transformed microorganism possessing an inositol-1-phosphoric acid synthase gene, inositol monophosphatase gene, myo-inositol dehydrogenase gene, and scyllo-inositol dehydrogenase gene.

Matters and embodiments mentioned with regard to the second aspect of the present invention are also true for the transformants of (9) above of the present invention. Therefore, they include the following:

(10) The transformed microorganism according to (9) above, further possessing a gene recombination or mutation to induce functional inositol monophosphatase overexpression or inositol monophosphatase activation;

(11) The transformed microorganism according to (9) or (10) above, being derived from a microorganism that does not have the ability to assimilate myo-inositol;

(12) The transformed microorganism according to any of (9) to (11) above, being derived from a bacterium selected from the group consisting of *Escherichia coli*, bacteria belonging to the genus *Bacillus*, bacteria belonging to the genus *Corynebacterium*, and bacteria belonging to the genus *Zymomonas*; and

(13) The transformed microorganism according to any of (10) to (12) above wherein the inositol monophosphatase overproduction is induced by, in the transformed microorganism:

a) introducing an exogenous inositol monophosphatase gene, b) increasing the number of copies of an endogenous inositol monophosphatase gene, c) introducing a mutation into a regulatory region of the endogenous inositol monophosphatase gene, d) replacing the regulatory region of the endogenous inositol monophosphatase gene with a high expression-inducing exogenous regulatory region, or e) deleting the regulatory region of the endogenous inositol monophosphatase gene;

(14) The transformed microorganism according to (13) above wherein the inositol monophosphatase overproduction is induced by introducing the exogenous inositol monophosphatase gene into the transformed microorganism; and

(15) The transformed microorganism according to any of (10) to (12) above wherein the inositol monophosphatase activation is induced by, ino the transformed microorganism:

f) introducing a mutation into an endogenous inositol monophosphatase gene, g) replacing all or part of the endogenous inositol monophosphatase gene, h) deleting part of the endogenous inositol monophosphatase gene, i) reducing other proteins that lower inositol monophosphatase activity, or j) reducing production of compounds that lower inositol monophosphatase activity.

Yet another aspect of the present invention is a novel scyllo-inositol derivative discovered to be produced in the culture of the above transformant. Specifically, the present invention also intends:

(16) a compound shown by the following structural formula:

[Chemical Formula 2]

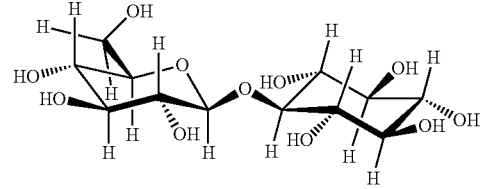

The scyllo-inositol derivative of the present invention can be decomposed by enzymes, for example, β-glucosidase (EC 3.2.1.21), capable of catalyzing a reaction that hydrolyzes β-glycoside bonds, and produces glucose and scyllo-inositol easily. The high water solubility demonstrated by the scyllo-inositol derivative of the present invention can be advantageous in such enzymatic reactions. Therefore, yet another aspect of the present invention is:

(17) a method for producing scyllo-inositol, the method being characterized in that the compound of (16) above is decomposed by an enzyme capable of catalyzing a reaction that hydrolyzes β-glycoside bonds, to produce scyllo-inositol.

The present invention is also:

(18) a composition containing scyllo-inositol and the compound of (16) above.

Advantages of the Invention

The present invention makes it possible to achieve more efficient industrial scyllo-inositol production through microbial culture techniques. The present invention also provides a novel scyllo-inositol derivative. Since it has very high water-solubility, this derivative can improve the concentration produced per batch in the production process and provides excellent handling when producing related products. The industrial productivity of scyllo-inositol can also be improved.

BRIEF DESCRIPTION OF THE DRAWINGS

FIG. 1 shows a coding region of INO1 gene (SEQ ID NO: 1).

FIG. 2 shows a coding region of suhB gene (SEQ ID NO: 3).

FIG. 3 shows a coding region of iolG gene (SEQ ID NO: 5).

FIG. 4 shows a coding region of iolW gene (SEQ ID NO: 7).

BEST MODE FOR CARRYING OUT THE INVENTION

Figure 5:
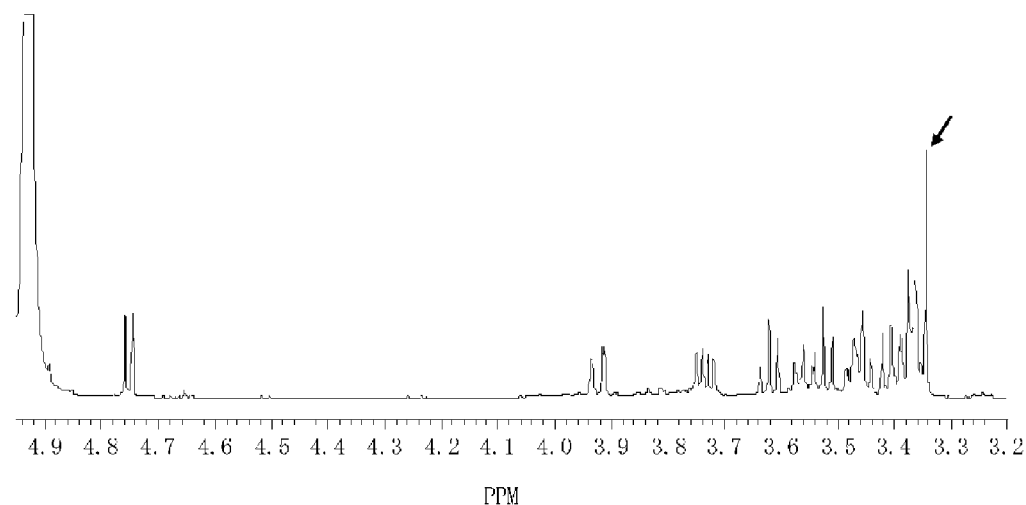
FIG. 5 is a $^1$H-NMR spectrum of the scyllo-inositol derivative of the present invention. In the figure, the peak shown by the arrow is from an impurity.

The first problem of the present invention is solved by fermenting a transformed microorganism possessing an inositol-1-phosphoric acid synthase gene, inositol monophosphatase gene, myo-inositol dehydrogenase gene, and scyllo-inositol dehydrogenase gene in a medium containing glucose or disaccharides or polysaccharides having glucose units as the carbon source or by bringing this transformant into contact with this carbon source. Namely, the transformed microorganism of the present invention has the capacity to convert a glucose substrate into scyllo-inositol and a derivative thereof by one-step fermentation by consecutive biosynthetic pathways newly constructed within the microorganism.

Typically, the biosynthetic pathway that converts a glucose substrate into the scyllo-inositol (or simultaneously produced scyllo-inositol derivative; the two together are sometimes referred to hereinafter as "scyllo-inositol of the present invention") of the present invention includes a partial pathway for conversion of the glucose substrate into myo-inositol, an important intermediate.

Specifically, in the case of a prokaryotic host, a partial pathway for myo-inositol biosynthesis can be made to function within the microorganism by causing the following catalytic activities to be expressed.

Activity 1: activity to produce glucose-6-phosphate from a suitable carbon source;

activity 2: activity to convert glucose-6-phosphate into myo-inositol-1-phosphate, that is, inositol-1-phosphoric acid synthase activity; and activity 3: phosphatase activity taking myo-inositol-1-phosphate as a substrate.

However, since glucose-6-phosphate that is the product of activity 1 is a metabolic intermediate universally produced by prokaryotic microorganisms, it is not essential to impart this activity to prokaryotic microorganisms. With regard to activity 3 as well, as far as the inventors know, endogenous inositol monophosphatase is expressed in the majority of prokaryotic microbial host cells suited to industrial production by conventional gene recombination techniques, or they have general monophosphatase activity capable of using myo-inositol-1-phosphate as a substrate.

On the other hand, as for activity 2, there are many examples of prokaryotic microorganisms that do not have an inositol-1-phosphoric acid synthase gene. Inositol-1-phosphoric acid synthase is believed to be responsible for a rate-limiting reaction in myo-inositol biosynthetic reactions (refer to Patent References 14 and 15). It was therefore thought to be necessary and sufficient to introduce an exogenous inositol-1-phosphoric acid synthase gene into the cell to construct a functional myo-inositol biosynthetic pathway within a prokaryotic microbial host.

However, in the co-pending Japanese Patent Application No. 2011-248438, the present inventors discovered unexpectedly that the myo-inositol production capacity is vastly improved by enhancing the inositol monophosphatase activity in transformants having an exogenous inositol-1-phosphoric acid synthase gene introduced as described above. Surprisingly enough, it also became clear that the transformants of the present invention produce very large amounts of scyllo-inositol predominantly while on the other hand producing a substantial amount of the scyllo-inositol derivative of present invention without virtually any myo-inositol being produced by enhancing their inositol monophosphatase activity, as in the examples below. Therefore, it is preferable to introduce a gene recombination or mutation to induce functional inositol monophosphatase overproduction or inositol monophosphatase activation in addition to introducing an exogenous inositol-1-phosphoric acid synthase gene as described above in the transformants of the present invention.

Regardless of whether or not the host microorganism has endogenous inositol monophosphatase activity, inducing overproduction of inositol monophosphatase within the cell of the transformed microorganism can enhance the inositol monophosphatase activity of the cell. Overproduction of inositol monophosphatase can preferably be induced by introducing an exogenous inositol monophosphatase gene into the transformed microorganism, but possibilities are not limited thereto. Furthermore, in this specification, the term "exogenous" is used to mean that a gene or nucleic acid sequence based on the present invention is introduced into a host in a case in which the host microorganism prior to transformation does not have the gene to be introduced by the present invention, in a case in which it substantially does not express the enzyme encoded by this gene, and in a case in which the amino acid sequence of this enzyme is encoded by a different gene, but endogenous enzyme activity comparable to that after transformation is not expressed.

Next, the following catalytic activities are imparted to the transformant of the present invention, that is, to a transformed microorganism having consecutive biosynthetic pathways capable of converting a glucose substrate into scyllo-inositol (or simultaneously produced scyllo-inositol derivative).

Activity 4: enzyme activity to convert myo-inositol into 2-keto-myo-inositol (myo-inosose; 2,3,4,5,6-pentahydroxycyclohexan-1-one); and activity 5: enzyme activity to convert 2-keto-myo-inositol into scyllo-inositol.

Examples of enzymes having activity 4 include myo-inositol dehydrogenase (enzyme no. E.C.1.1.1.18) which oxidizes myo-inositol in the presence of $NAD^+$, for example. Examples of enzymes having activity 5 include scyllo-inositol dehydrogenase which oxidizes scyllo-inositol in the presence of $NADP^+$, for example. Namely, scyllo-inositol dehydrogenase that can be used in the present invention is capable of converting 2-keto-myo-inositol into scyllo-inositol in the presence of NADPH, for example.

The transformant of the present invention can be made using various host microbial cells. Using a prokaryotic microorganism as a host in particular is highly attractive for the application of synthetic biology techniques since it allows a biosynthetic pathway of the scyllo-inositol of the present invention to be newly constructed (that is, with no effect of an existing endogenous pathway) within the host cell. Prokaryotic microorganisms that can be given as examples are bacteria belonging to the genera *Escherichia, Pseudomonas, Bacillus, Geobacillus, Methanomonas, Methylobacillus, Methylophilus, Protaminobacter, Methylococcus, Corynebacterium, Brevibacterium, Zymomonas*, and *Listeria*. Nonlimiting examples of prokaryotic microorganisms suited to industrial fermentative production include *Escherichia coli*, bacteria belonging to the genus *Bacillus*, bacteria belonging to the genus *Corynebacterium*, and bacteria belonging to the genus *Zymomonas*. *Escherichia coli* is an especially preferred example of a host microorganism of the present invention because of its rapid growth capacity and ease of fermentation control. Cell lines that can be utilized as host cells of the present invention may be wild types in the ordinary sense or may be auxotrophic mutants or antibiotic-resistant mutants. Cell lines that can be utilized as host cells of the present invention may also be already transformed so as to have various marker genes related to the mutations as mentioned above. These mutations and genes make it possible to provide properties beneficial to the production, maintenance, and control of the transformants of the present invention. Preferably, the use of a strain presenting resistance to chloramphenicol, ampicillin, kanamycin, tetracycline, and other such antibiotics makes it possible to produce the scyllo-inositol of the present invention easily.

As was mentioned above, the scyllo-inositol biosynthetic pathway that the transformant of the present invention should have includes a partial pathway for converting the glucose substrate into myo-inositol, an important intermediate. Since inositol-1-phosphoric acid synthase is believed to be responsible for a rate-limiting reaction in myo-inositol biosynthesis, as was also mentioned above, the transformant of the present invention must express inositol-1-phosphoric acid synthase activity as the first bioactivity. Since there are many examples of prokaryotic microorganisms that do not have an inositol-1-phosphoric acid synthase gene, an exogenous inositol-1-phosphoric acid synthase gene is usually introduced expressibly into the cell of the transformant of the present invention. Inositol-1-phosphoric acid synthase genes are known (for example, GenBank Accession Nos. AB032073, AF056325, AF071103, AF078915, AF120146, AF207640, AF284065, BC111160, L23520, U32511), and any of these can be used for the purposes of the present invention. The INO1 gene (SEQ ID NO: 1) gene derived from yeast is a well-known example of an inositol-1-phosphoric acid synthase gene and can be used appropriately in the present invention as well. However, inositol-1-phosphoric acid synthase genes that can be utilized in the present invention are not limited to those derived from yeasts and may be derived from other eukaryotic microorganisms and other organisms or may be artificially synthesized, as long as they are capable of expressing substantial inositol-1-phosphase synthase activity within the host microbial cells.

Therefore, inositol-1-phosphoric acid synthase genes that can be utilized for purposes of the present invention may have any mutations capable of occurring in the natural world and artificially introduced mutations and modifications as long as they are capable of expressing substantial inositol-1-phosphase synthase activity within the transformed microorganism. For example, the presence of excess codons (redundancy) is known in various codons that encode specific amino acids. Alternate codons that are finally translated into the same amino acids may therefore also be utilized in the present invention. In other words, since the genetic code degenerates, multiple codons can be used to encode certain specific amino acids, and the amino acid sequence can therefore be encoded by a DNA oligonucleotide similar to any one set. While only one member of that set is identical to the genetic sequence of the native enzyme, even mismatched DNA oligonucleotides can hybridize with the native sequence under suitable stringent conditions (for example, hybridization by 3×SSC, 68° C.; washing by 2×SSC, 0.1% SDS, and 68° C.), and DNA that encodes the native sequence can be identified and isolated. Such genes can also be utilized in the present invention. In particular, since virtually all organisms are known to use subsets of specific codons (optimal codons) preferentially (Gene, Vol. 105, pp. 61-72, 1991, and the like), "codon optimization" in accordance with the host microorganism can also be useful in the present invention.

Those skilled in the art will appreciate that, in producing the transformant of the present invention as well, a more stable, higher level of inositol-1-phosphoric acid synthase activity is obtained by introducing an inositol-1-phosphoric acid synthase gene into the host microbial cells as an "expression cassette." In this specification, "expression cassette" means a nucleotide containing a nucleic acid sequence that regulates transcription and translation functionally linked to the nucleic acid to be expressed or the gene to be expressed. Typically, an expression cassette of the present invention contains a promoter sequence 5' upstream from the coding sequence and a terminator sequence 3' downstream from the sequence. Sometimes it contains a further normal regulatory element in a functionally linked state. In such cases, the nucleic acid to be expressed or the gene to be expressed is introduced expressibly into the host microorganism.

A promoter is defined as a DNA sequence that links RNA polymerase to DNA and initiates RNA synthesis, regardless of whether it is a constitutive promoter or a regulatory promoter. A strong promoter means a promoter that initiates mRNA synthesis at high frequency and is also preferably used in producing the transformant of the present invention. A lac promoter, trp promoter, TAC or TRC promoter, major operator and promoter regions of λ phage, fd coat protein control region, promoters for a glycolytic enzyme (for example, 3-phosphoglycerate kinase, glyceraldehyde-3-phosphate dehydrogenase), glutamate decarboxylase A, serine hydroxymethyl transferase, and the like can be utilized in accordance with the properties and the like of the host cells. Examples of regulatory elements other than promoter and terminator sequences include selection markers, amplification signals, replication origins, and the like. Suitable regulatory sequences are listed, for example, in "Gene Expression Technology Methods in Enzymology 185," Academic Press (1990).

The expression cassette explained above is incorporated, for example, into a vector consisting of a plasmid, phage, transposon, IS element, phasmid, cosmid, linear or circular DNA, or the like, and inserted into the host microorganism. Plasmids and phages are preferred. These vectors may be autonomously replicated in the host microorganism or may be replicated chromosomally. Suitable plasmids include, for example, *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III113-B1, λgt11 or pBdCI; *Bacillus* pUB110, pC194 or pBD214; *Corynebacterium* pSA77 or pAJ667; and the like. Plasmids and the like that can also be used in addition to these are listed in "Cloning Vectors," Elsevier, 1985. The expression cassette can be introduced into the vector by ordinary methods, including excision by suitable restriction enzymes, cloning, and ligation.

After having constructed a vector having an expression cassette as discussed above, coprecipitation, protoplast fusion, electroporation, retrovirus transfection, and other such ordinary cloning methods and transfection methods are used as methods that can be used to introduce the vector into the host microorganism. Examples of these are listed in "Current Protocols in Molecular Biology," F. Ausubel et al., Publ. Wiley Interscience, New York, 1997 or Sambrook et al., "Molecular Cloning: Laboratory Manual," 2$^{nd}$ edition, Cold Spring Harbor Laboratory, Cold Spring Harbor Laboratory Press, Cold Spring Harbor, N.Y., 1989.

Next, the second bioactivity that the transformant of the present invention should have is inositol monophosphatase activity. This inositol monophosphatase activity is also required to convert the glucose substrate into the intermediate myo-inositol. However, as was mentioned above, since the majority of prokaryotic microbial host cells suited to industrial production by conventional gene recombination techniques express endogenous inositol monophosphatase or have general monophosphatase activity capable of using myo-inositol-1-phosphate as a substrate, there is often no need to introduce this enzyme activity into the transformant of the present invention. Nonetheless, the transformant of the present invention more preferably presents enhanced inositol monophosphatase. Specifically, it was unexpectedly made clear that the scyllo-inositol-producing transformant of the present invention not only produces virtually no myo-inositol while producing a very large amount of scyllo-inositol predominantly but also notably produces a scyllo-inositol derivative by enhancing this inositol monophosphatase activity. Therefore, a preferred aspect of the present invention includes inducing overproduction of inositol monophosphatase within the scyllo-inositol-producing transformant.

The inositol monophosphatase intended in the present invention includes proteins capable of substantially hydrolyzing inositol-1-phosphate by presenting phosphoric monoester hydrolase activity capable of acting on a wide range of substrates in addition to those presenting high substrate specificity for inositol-1-phosphate. For example, inositol-1-monophosphatase is known as a typical inositol monophosphatase, and this gene (suhB gene) from many organisms has been published in GenBank Accession Nos. ZP_04619988, YP_001451848, and the like. In particular, the use of a suhB gene from *E. coli* (SEQ ID NO: 3: AAC75586 (MG1655)) is convenient when *E. coli* is used as the host cell.

The third bioactivity that the transformant of the present invention should have is myo-inositol dehydrogenase activity. This enzyme typically converts myo-inositol into 2-keto-myo-inositol in the presence of NAD$^+$ by the following reaction.

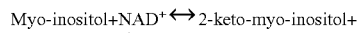

Myo-inositol+NAD$^+$ ⇌ 2-keto-myo-inositol+ NADH+H$^+$     [Chemical Formula 3]

Various myo-inositol dehydrogenase genes are known and can be utilized. For example, JP Kokai 6-7158 describes an enzyme (EC 1.1.1.18) from bacteria of the genus *Bacillus* capable of converting myo-inositol into 2-keto-myo-inositol in the presence of NAD$^+$ and a nucleic acid sequence that encodes the enzyme. In addition, Patent Reference 5 discloses NAD$^+$-independent myo-inositol dehydrogenase, and this enzyme can also be used in production of the transformant of the present invention. In particular, it is convenient to use an iolG gene (SEQ ID NO: 5 below) from *Bacillus subtilis* NBRC13719.

[Chemical Formula 4]

(SEQ ID NO: 5)

atgagtttacgtattggcgtaattggaactggagc aatcggaaaagaacatattaaccgtatcacgaaca agctgtcaggcgcggaaattgtagctgtaacggat gttaatcaagaagctgcacaaaaggtcgttgagca ataccaattaaacgcgacggtttatccgaatgatg acagcttgcttgcagacgaaaatgtagacgctgtt ttagtgacaagctgggggcctgcgcatgagtcaag cgtgctgaaagcgattaaagcccagaaatatgtgt tctgtgaaaaaccgctcgcgacaacggctgaagga tgcatgcgcattgtcgaagaagaaatcaaagtggg caaacgccttgttcaagtcggcttcatgcgccgtt atgacagcggttacgtacagctgaaagaagcgctc gataatcatgtcatcggcgagcctcttatgattca ctgcgcgcaccgcaacccgactgtaggagataact atacaacggatatggctgtagtcgacacgcttgtt catgaaattgacgtgctccactggctcgtcaatga tgactacgagtccgttcaagtcatctatccgaaaa aatcaaaaaacgcgcttccacatttaaaagatccg caaatcgtcgtgattgaaacaaaaggcggtatcgt catcaatgctgaaatctatgtgaactgtaaatacg gctatgacattcaatgtgaaatcgtcggagaagac

```
ggcatcatcaagcttcccgagccatcaagcatcag cttgagaaagaaggcagattcagcactgatattt tgatggattggcagagacgctttgtcgctgcgtat gatgtggaaatccaagactttattgattcgattca aaagaaaggcgaggtcagcggaccgacggcatggg acggctatattgctgctgtcacgactgacgcgtgt gtaaaagcccaggaatctggacaaaaagaaaaggt tgaattgaaggaaaaaccggaattctatcaatctt ttacaacagttcaaaactaa
```

The fourth bioactivity that the transformant of the present invention should have is scyllo-inositol dehydrogenase activity. This enzyme typically converts scyllo-inositol into 2-keto-myo-inositol in the presence of $NADP^+$ by the following reaction, and selectively reduces 2-keto-myo-inositol into scyllo-inositol in the presence of NADPH. The latter reaction is utilized within the transformant of the present invention.

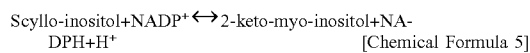
[Chemical Formula 5]

Various scyllo-inositol dehydrogenase genes are known and can be utilized. Patent Reference 5 discloses scyllo-inositol dehydrogenase from *E. coli*, bacteria of the genus *Acetobacter*, bacteria of the genus *Bacillus*, bacteria of the genus *Agrobacterium*, and bacteria of the genus *Xanthomonas* and related amino acid sequences. In particular, the use of an iolW gene (SEQ ID NO: 7 below) from *Bacillus subtilis* NBRC13719 is convenient.

[Chemical Formula 6]
(SEQ ID NO: 7)
```
atgataacgcttttaaaggggagaagaaaagtgga tacgatcaaggttggaatattaggatacggattgt ccggttctgtttttcacgggccgctgctggatgtt ctggatgaatatcaaatcagcaaaatcatgacatc acggacagaagaagtgaaacgggattttccagatg ctgaggttgtacatgagcttgaagaaatcacaaat gaccctgccattgagcttgtcattgtcaccacccc gagcggccttcattacgagcatactatggcatgca tacaggccggaaacatgttgtgatggaaaaacca atgacagcaacggccgaagaggggaaacattaaa aagggctgccgatgaaaaaggcgtattattaagcg tatatcataaccgacgctgggataacgattttta acgattaaaagctgatctctgagggatcccttga agatatcaatacatatcaagtttcctataaccgct acagacctgaagttcaagcgcggtggcgggaaaaa gaaggcactgccactggtacgctgtatgatctcgg ctcccacatcatagaccaaaccctgcatttgtttg ggatgcctaaagccgtgactgcaaacgtgatggcc cagcgggaaaatgccgaaacggttgactattttca tttaaccctggattatggcaagcttcaagccattc tatacggaggatcaatcgttccggcaaacggacct cgttatcaaatccatggaaaagattctagctttat caaatatggaattgacggacaggaagacgcactca gagcgggaagaaaaccagaggatgacagctggggt gcggatgttccggagttttacggaaagcttacaac cattcgtggctccgacaaaaaaacagaaacgattc catcagtaaatggctcctaccttacttattaccgt aaaatagcggaaagcatacgagaaggtgctgcgct gccagtcactgctgaggaaggtattaatgtcatcc gcatcattgaagccgcgatggaaagcagtaaagag aaacgaaccattatgctggagcactaa
```

Those skilled in the art will readily appreciate that the above explanation of mutation, modification, and codon optimization, expression cassette, promoter and other regulator sequences and plasmids, and transformation thereby given with regard to the inositol-1-phosphoric acid synthase gene holds true for all of the above inositol monophosphatase genes, myo-inositol dehydrogenase genes, and scyllo-inositol dehydrogenase genes. Therefore, the transformant of the present invention possesses three expression cassettes: an expression cassette containing nucleic acid to encode inositol-1-phosphoric acid synthase, an expression cassette containing nucleic acid to encode myo-inositol dehydrogenase, and an expression cassette containing nucleic acid to encode scyllo-inositol dehydrogenase, in which case an endogenous inositol monophosphatase gene is present in the transformant of the present invention. The transformant of the present invention preferably possesses an expression cassette containing nucleic acid having a nucleotide sequence shown by SEQ ID NO: 1, an expression cassette containing nucleic acid having a nucleotide sequence shown by SEQ ID NO: 5, and an expression cassette containing nucleic acid having a nucleotide sequence shown by SEQ ID NO: 7.

The above three expression cassettes may be placed on one vector and transfected into a host microorganism. Alternatively, a vector on which any two expression cassettes have been placed and a vector on which the remaining expression cassette has been placed may be co-transfected into a host microorganism, or three vectors on each of which one expression cassette each has been placed may be co-transfected into a host microorganism. Any one or more of the above three expression cassettes may also be incorporated into the genome of a host microorganism, and the remaining expression cassettes may be present in the transformant as plasmids. For example, it is also possible to transfect a plasmid on which an expression cassette containing nucleic acid to encode myo-inositol dehydrogenase and an expression cassette containing nucleic acid to encode scyllo-inositol dehydrogenase have been placed into *E. coli* AKC-017 (deposited as FERM P-22180 on Oct. 25, 2011 at the Incorporated Administrative Agency National Institute of Technology and Evaluation, Patent Microorganisms Depositary. International Accession No.: FERM BP-11513) obtained by incorporating an expression cassette containing nucleic acid for encoding inositol-1-phosphoric acid synthase (INO1) on a chromosome.

In addition, as has been stated repeatedly, it is particularly preferable that the transformant of the present invention presents enhanced inositol monophosphatase. Therefore, the transformant of the present invention preferably possesses an expression cassette containing nucleic acid to encode inositol monophosphatase in addition to the above three expression cassettes. Therefore, examples of more preferred transformants of the present invention include transformants possessing an expression cassette containing nucleic acid having a nucleotide sequence shown by SEQ ID NO: 1, an expression cassette containing nucleic acid having a nucleotide sequence shown by SEQ ID NO: 3, an expression cassette containing nucleic acid having a nucleotide sequence shown by SEQ ID NO: 5, and an expression cassette containing nucleic acid having a nucleotide sequence shown by SEQ ID NO: 7.

The above four expression cassettes may be placed on one vector and transfected into a host microorganism. Alternatively, a vector on which any two or more expression cassettes have been placed and a vector on which the remaining expression cassettes have been placed may be co-transfected into a host microorganism, or four vectors on each of which one expression cassette each has been placed may be co-transfected into a host microorganism. Any one or more of the above four expression cassettes may also be incorporated into the genome of a host microorganism, and the remaining expression cassettes may be present in the transformant as plasmids. For example, it is also possible to transfect a plasmid on which an expression cassette containing nucleic acid to encode myo-inositol dehydrogenase and an expression cassette containing nucleic acid to encode scyllo-inositol dehydrogenase have been placed into E. coli AKC-018 (deposited as FERM P-22181 on Oct. 25, 2011 at the Incorporated Administrative Agency National Institute of Technology and Evaluation, Patent Microorganisms Depositary. International Accession No.: FERM BP-11514) having both an expression cassette containing nucleic acid for encoding inositol-1-phosphoric acid synthase (INO1) and an expression cassette containing nucleic acid for encoding inositol monophosphatase (subB) on a chromosome.

Furthermore, in connection with methods of inducing enhanced inositol monophosphatase activity in a preferred transformant of the present invention, overproduction of the inositol monophosphatase can also be induced by increasing the number of copies of an endogenous inositol monophosphatase gene; introducing a mutation into a regulatory region of the endogenous inositol monophosphatase gene; replacing the regulatory region of the endogenous inositol monophosphatase gene with a high expression-inducing exogenous regulatory region, and deleting the regulatory region of the endogenous inositol monophosphatase gene. Specifically, overexpression of inositol monophosphatase can be achieved by transforming the host microorganism by a construct containing the endogenous inositol monophosphatase gene or an expression cassette in which a suitable regulatory region has been added to a coding region of this endogenous gene to substantially increase the number of copies of this inositol monophosphatase gene within this transformant in comparison to the original host cell or, with respect to an original host cell having an endogenous inositol monophosphatase gene, conducting chromosomal mutation, addition, and deletion by known gene recombination techniques or introducing random mutation on a chromosome using a mutagen or the like. The overproduction of inositol monophosphatase can be confirmed using known SDS-PAGE analytical methods, and the like.

Another embodiment of the present invention for enhancing inositol monophosphatase activity includes inducing activation of inositol monophosphatase in the transformant of the present invention. Examples of techniques used for this purpose are 1) introducing a mutation into an endogenous inositol monophosphatase gene, 2) replacing all or part of the endogenous inositol monophosphatase gene, 3) deleting part of the endogenous inositol monophosphatase gene, 4) reducing other proteins that lower inositol monophosphatase activity, and/or 5) reducing production of compounds that lower inositol monophosphatase activity.

With regard to the above methods 1)-5) to enhance inositol monophosphatase activity, inositol monophosphatase having enhanced inositol monophosphatase activity can be obtained by evaluating the activity of inositol monophosphatase encoded by this gene after having subjected the inositol monophosphatase gene to mutation, addition, or deletion.

The transformants obtained as described above are cultured and maintained under conditions suited to the growth and/or maintenance of the transformants to produce the scyllo-inositol of the present invention. Suitable medium compositions, culture conditions, and culture times for transformants derived from various host microbial cells are known to those skilled in the art.

The medium may be a natural, semisynthetic, or synthetic medium containing one or more carbon sources, nitrogen sources, inorganic salts, vitamins, and, sometimes, trace elements or vitamins, and other such trace components. However, it goes without saying that the medium used must properly satisfy the nutrient requirements of the transformants to be cultured. Media that can be used in the present invention also contain glucose or disaccharides or polysaccharides having glucose units to cause de novo scyllo-inositol biosynthesis and biosynthesis of the scyllo-inositol derivative to advance easily by the transformants of the present invention. Many disaccharides or polysaccharides having glucose units are known to those skilled in the art. Nonlimiting examples include sucrose, maltose, lactose, starch, and cellulose. Since these are contained in large amounts in rice bran, molasses, decomposed corn solution, decomposed cellulose solution, and other such biomasses, it is preferable to use a medium having these natural sources as a carbon source. When the transformants express useful additional traits, for example, when they have resistance markers for antibiotics, the medium may contain the corresponding antibiotics. This reduces the risk of contamination by foreign bacteria during fermentation. Furthermore, when the host microorganisms cannot assimilate cellulose or other such carbon sources, the host microorganisms can be adapted to production of scyllo-inositol and its derivative using these carbon sources by introducing an exogenous gene or other such known genetic engineering techniques. Examples of exogenous genes include cellulase genes, amylase genes, and the like.

Culture may be either by batch or continuous. In either case, it may be in the form of supplying additional above-mentioned carbon source and the like at a suitable point in time during culture. Culture should also be continued while maintaining a suitable temperature, oxygen concentration, pH, and the like. A suitable culture temperature for transformants derived from common microbial host cells is usually 15-45° C., preferably in the 25-37° C. range. When the host microorganism is aerobic, shaking (flask culture and the like), stirring/aeration (jar fermenter culture and the like)

is necessary to assure a suitable oxygen concentration during fermentation. These culture conditions are easy to establish for those skilled in the art.

Methods of refining scyllo-inositol or its derivative from the above culture may be suitable combinations of refining techniques known to those skilled in the art. In the case of transformants of prokaryotic microbial host cells, the scyllo-inositol of the present invention is present in the culture supernatant or in the cells, and may be extracted from the cultured cells if necessary. In the case of extraction from cultured cells, for example, the culture is centrifuged to separate the supernatant and cells, and the cells can be broken down by surfactant, organic solvent, enzyme, or the like while utilizing a homogenizer. Typical methods of refining scyllo-inositol and its derivative from the culture supernatant and sometimes from a cell extraction liquid include deproteination utilizing protein precipitation by pH adjustment or the like, removal of impurities by adsorption utilizing activated carbon, chromatography utilizing ion-exchange resin or the like, and other such refining processes. A solid obtained by drying a fraction separated by chromatography may also be recrystallized, for example, from a water-ethanol system. As shall be apparent, some steps may be omitted or additional chromatography, recrystallization, and the like may be implemented depending on the target purity of the product.

The scyllo-inositol derivative pertaining to the second problem of the present invention has a structure consisting of glucose residues and scyllo-inositol residues linked by β1→4 bonds and is represented by the following structural formula.

[Chemical Formula 7]

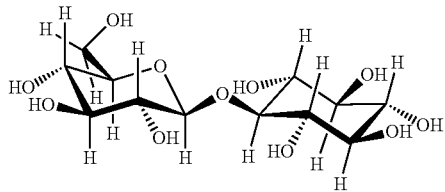

The above compound is novel and can also be called 1-O-β-D-glucopyranosyl-scyllo-inositol.

As in the examples discussed below, the scyllo-inositol derivative of the present invention can be decomposed easily by an enzyme capable of catalyzing a reaction that hydrolyzes β-glycoside bonds, for example, β-glucosidase (EC 3.2.1.21), easily producing glucose and scyllo-inositol. Therefore, scyllo-inositol can be produced by causing this enzyme to act on the scyllo-inositol derivative of the present invention.

In particular, the scyllo-inositol derivative of the present invention, as will be discussed below, presents at least four times greater water solubility (25° C., W/V) than the original scyllo-inositol. Since the scyllo-inositol derivative of the present invention can be produced and treated at high concentration in an aqueous solution, producing scyllo-inositol by obtaining the scyllo-inositol derivative of the present invention and treating it enzymatically has many advantages. Such methods are therefore one preferred method of utilizing the scyllo-inositol derivative of the present invention.

In enzymatic decomposition of the scyllo-inositol derivative of the present invention by β-glucosidase or the like to produce scyllo-inositol as described above, an appropriate amount of enzyme is added to a solution of the scyllo-inositol derivative of the present invention obtained by water or buffer (acetate buffer, phosphate buffer, or the like), and the solution may be incubated using conditions and time suited to the enzymatic reaction. β-Glucosidases that can be used for this purpose are marketed, and all can be used. Cellobiase (Sigma) from molds of the genus *Aspergillus*, for example, may be utilized. The amount of enzyme added may be decided as appropriate based on the concentration of the scyllo-inositol derivative of the present invention in the solution and other such factors while referring to the manufacturer's instructions. The pH during reaction is generally in the pH 4.0-9.0 range, but in essence should be the optimum pH for the enzyme used. The temperature during reaction should also be within the optimum temperature range of the enzyme used, for example, a range of about 20-50° C. The reaction may be continued until the time when basically all of the scyllo-inositol derivative of the present invention has been converted into scyllo-inositol while quantitatively tracing the decomposition rate of the scyllo-inositol derivative of the present invention. Scyllo-inositol may then be separated from the reaction solution by recrystallization or the like.

Furthermore, as in the examples discussed below, the scyllo-inositol productivity can be further increased when the transformant of the present invention is cultured under conditions that produce a substantial amount of scyllo-inositol derivative of the present invention together with scyllo-inositol by treating the culture as is of this transformant by the above-mentioned enzyme or by enzyme treatment after having crudely refined the culture by deproteination treatment or activated charcoal treatment.

Use as an active ingredient or functional component of drugs, foods, cosmetics, and the like is a potential application of the scyllo-inositol derivative of the present invention. In other words, since the bioactivity of scyllo-inositol is being clarified, as was mentioned above, and scyllo-inositol is produced easily by enzymatic decomposition of the scyllo-inositol derivative of the present invention, addition of the scyllo-inositol derivative of the present invention itself to drugs and the like, with the expectation that the scyllo-inositol derivative of the present invention is enzymatically decomposed within the body to produce scyllo-inositol, is a very interesting mode of use of the present invention.

Those skilled in the art who have been provided with the above explanation can implement the present invention adequately. Examples are given below for the sake of further explanation. Therefore, the present invention is not limited to these examples. Furthermore, the nucleotide sequences in this specification are described in the direction from 5' to 3' unless stated otherwise.

EXAMPLES

Example 1

Scyllo-Inositol do Novo Production by a Transformant without Enhancement of Inositol Monophosphatase Activity In this example, a transformed microorganism of the present invention possessing three expression cassettes: an expression cassette containing nucleic acid encoding inositol-1-phosphoric acid synthase, an expression cassette containing nucleic acid encoding myo-inositol dehydrogenase, and an expression cassette containing nucleic acid encoding scyllo-inositol dehydrogenase, was produced, and its capacity to produce scyllo-inositol was investigated.

1-a) Inositol-1-Phosphoric Acid Synthase Expression Cassette

The cells were collected from the isolated distillery yeast culture broth, and the genomic DNA was extracted using Nucleo Spin Tissue (product name, manufactured by Macherey-Nagel). Using the extracted genomic DNA as a template, PCR amplification (PrimeSTAR Max DNA Polymerase (product name, manufactured by Takara Bio), reaction conditions: 98° C. 10 sec, 55° C. 5 sec, 72° C. 20 sec, 28 cycles) was carried out by the following primers, and the coding region of the INO1 gene (SEQ ID NO: 1) was cloned.

[Chemical Formula 8]
(SEQ ID NO: 9)
Forward: atgacagaagataatattgctc (SEQ ID NO: 10)
Reverse: ttacaacaatctctcttcg Next, the ino1 coding region obtained was inserted transcribably downstream of a promoter of the following sequence.

[Chemical Formula 9]
Promoter:
(SEQ ID NO: 11)
ctcaagcccaaaggaagagtgaggcga gtcagtcgcgtaatgcttaggcacaggattgattt gtcgcaatgattgacacgattccgcttgacgctgc gtaaggttttttgtaatttttacaggcaacctttat tcactaacaaatagctggtggaa Specifically, a terminator sequence and the above promoter sequence were inserted at the multicloning site of plasmid pNFP-A51 (deposited as FERM P-22182 on Oct. 25, 2011 at the Incorporated Administrative Agency National Institute of Technology and Evaluation, Patent Microorganisms Depositary. International Accession No.: FERM BP-11515). The ino1 coding region cloned as described above was ligated downstream of the promoter sequence introduced, and pNFP-D78 was constructed. The pNFP-D78 constructed was transfected into *E. coli* AKC-016 (deposited as FERM P-22104 on Apr. 20, 2011 at the Incorporated Administrative Agency National Institute of Technology and Evaluation, Patent Microorganisms Depositary. International Accession No.: FERM BP-11512) by the calcium chloride method (refer to Genetic Engineering Laboratory Notebook (Part I), by Takaaki Tamura, Yodosha). High expression of inositol-1-phosphoric acid synthase was confirmed in the soluble fraction of this *E. coli* by SDS-PAGE.

1-b) Myo-Inositol Dehydrogenase Expression Cassette

*Bacillus subtilis* (NBRC13719) was shake-cultured at 30° C. in LB medium (2 mL). After culture had been completed, the cells were collected from the culture broth, and the genomic DNA was extracted using Nucleo Spin Tissue (product name, manufactured by Macherey-Nagel). Using the extracted genomic DNA as a template, PCR amplification (PrimeSTAR Max DNA Polymerase (product name, manufactured by Takara Bio), reaction conditions: 98° C. for 10 sec, 55° C. for 5 sec, and 72° C. for 20 sec, 28 cycles) was carried out by the following primers, and the coding region of the iolG gene (SEQ ID NO: 5) was cloned.

[Chemical Formula 10]
(SEQ ID NO: 12)
Forward: atgagtttacgtattggcgtaa (SEQ ID NO: 13)
Reverse: ttagttttgaactgttgtaaaagattg The iolG coding region obtained was inserted transcribably downstream of a promoter of SEQ ID NO: 11. Specifically, a terminator sequence and the above promoter sequence were inserted at the multicloning site of the above pNFP-A51. The iolG coding region cloned as described above was ligated downstream of the promoter sequence introduced, and pNFP-J22 was constructed. The pNFP-J22 constructed was transfected into *E. coli* FERM P-22104 by the calcium chloride method (refer to Genetic Engineering Laboratory Notebook (Part I), by Takaaki Tamura, Yodosha). High expression of myo-inositol dehydrogenase was confirmed in the soluble fraction of this *E. coli* by SDS-PAGE.

1-c) Scyllo-Inositol Dehydrogenase Expression Cassette

*Bacillus subtilis* (NBRC13719) was shake-cultured at 30° C. in LB medium (2 mL). After culture had been completed, the cells were collected from the culture broth, and the genomic DNA was extracted using Nucleo Spin Tissue (product name, manufactured by Macherey-Nagel). Using the extracted genomic DNA as a template, PCR amplification (PrimeSTAR Max DNA Polymerase (product name, manufactured by Takara Bio), reaction conditions: 98° C. for 10 sec, 55° C. for 5 sec, and 72° C. for 20 sec, 28 cycles) was carried out by the following primers, and the coding region of the iolW gene (SEQ ID NO: 7) was cloned.

[Chemical Formula 11]
(SEQ ID NO: 14)
Forward: atgataacgcttttaaagggg (SEQ ID NO: 15)
Reverse: ttagtgctccagcataatgg The iolW coding region obtained was inserted transcribably downstream of a promoter of SEQ ID NO: 11. Specifically, a terminator sequence and the above promoter sequence were inserted at the multicloning site of the above pNFP-A51. The iolW coding region cloned as described above was ligated downstream of the promoter sequence introduced, and pNFP-J36 was constructed. The pNFP-J36 constructed was transfected into *E. coli* FERM P-22104 by the calcium chloride method (refer to Genetic Engineering Laboratory Notebook (Part I), by Takaaki Tamura, Yodosha). High expression of scyllo-inositol dehydrogenase was confirmed in the soluble fraction of this *E. coli* by SDS-PAGE.

1-d) Construction of a Plasmid for Transformation pNFP-D78 was digested by Sal I, blunted, and the 5' end dephosphorylated. The iolG expression cassette in pNFP-J22 and the iolW expression cassette in pNFP-J36 were cloned, and the two expression cassettes were ligated into pNFP-D78. A plasmid having an INO1 expression cassette and an iolG expression cassette and iolW expression cassette in the forward direction ligated in pNFP-D78 was obtained.

1-e) Scyllo-Inositol Production by Transformants Transfected by an Expression Cassette-Containing Plasmid A plasmid constructed according to the procedure described above was transfected into *E. coli* AKC-016

(deposited as FERM P-22104 on Apr. 20, 2011 at the Incorporated Administrative Agency National Institute of Technology and Evaluation, Patent Microorganisms Depositary. International Accession No.: FERM BP-11512) by the calcium chloride method (refer to Genetic Engineering Laboratory Notebook (Part I), by Takaaki Tamura, Yodosha).

The transformant obtained was cultured for one day at 37° C. on LB plates containing ampicillin (100 mg/L) to form colonies. Two milliliters of LB medium containing ampicillin (100 mg/L) was placed in a 15 mL test tube and inoculated by a platinum loop with colonies from the above plate. Culture was carried out at 37° C. for 3-5 hours at 180 rpm until OD (600 nm) reached approximately 0.5. This was taken as preculture broth for the main culture.

A quantity of 2 g/L of glucose and 30 mL of LB medium containing 100 mg/L of ampicillin were placed in a 150 mL flask; 0.6 mL of preculture broth was added, and the main culture (scyllo-inositol production test) was conducted. The culture conditions were as follows: Culture temperature 32° C.; stirring 180 rpm; culture time 16.5 h.

The above culture broth was centrifuged at 4° C. for 10 min at 10,000×g, and the supernatant was collected. The scyllo-inositol concentration in the culture supernatant was measured. Specifically, the scyllo-inositol concentration in the culture supernatant was assayed by HPLC (detector: RI, column temperature: 70° C., flow rate: 1 mL/min,) linked to KS-G (guard column), Sugar KS-801, and Sugar KS-802 (all trade names, manufactured by Showa Denko K.K.). The results of assay clarified that 0.15 g/L of scyllo-inositol was produced in the culture supernatant and that the glucose was completely consumed. This results shows that the transformed microorganism of the present invention possessing three expression cassettes: an expression cassette containing nucleic acid encoding inositol-1-phosphoric acid synthase, an expression cassette containing nucleic acid encoding myo-inositol dehydrogenase, and an expression cassette containing nucleic acid encoding scyllo-inositol dehydrogenase, and having an endogenous inositol monophosphatase gene (that is, unenhanced inositol monophosphatase) produced scyllo-inositol from glucose directly by a one-step procedure.

Example 2

Scyllo-Inositol De Novo Production by a Transformant Having Enhanced Inositol Monophosphatase Activity In this example, a transformed microorganism of the present invention possessing four expression cassettes: an expression cassette containing nucleic acid encoding inositol-1-phosphoric acid synthase, an expression cassette containing nucleic acid encoding inositol monophosphatase, an expression cassette containing nucleic acid encoding myo-inositol dehydrogenase, and an expression cassette containing nucleic acid encoding scyllo-inositol dehydrogenase, was produced, and its capacity to produce scyllo-inositol was investigated.

2-a) Inositol Monophosphatase Expression Cassette

E. coli W3110 (NBRC12713) was shake-cultured at 37° C. in LB medium (2 mL). After culture had been completed, the cells were collected from the culture broth, and the genomic DNA was extracted using Nucleo Spin Tissue (product name, manufactured by Macherey-Nagel). Using the extracted genomic DNA as a template, PCR amplification (PrimeSTAR Max DNA Polymerase (product name, manufactured by Takara Bio), reaction conditions: 98° C. for 10 sec, 55° C. for 5 sec, and 72° C. for 20 sec, 28 cycles) was carried out by the following primers, and the coding region of the suhB gene (SEQ ID NO: 3) was cloned.

[Chemical Formula 12]

(SEQ ID NO: 16)
Forward: atgcatccgatgctgaac (SEQ ID NO: 17)
Reverse: ttaacgcttcagagcgtcg The suhB coding region obtained was inserted transcribably downstream of a promoter of the following sequence.

[Chemical Formula 13]
Promoter:
(SEQ ID NO: 18)
gtcgtttttctgcttaggatttgtta tttaaattaagcctgtaatgccttgcttccattgc ggataaatcctacttttttattgccttcaaataaa tttaaggagttc Specifically, a terminator sequence and a promoter sequence of SEQ ID NO: 18 were inserted at the multicloning site of the above pNFP-A51. The suhB coding region cloned as described above was ligated downstream of the promoter sequence introduced, and pNFP-A54 was constructed. The pNFP-A54 constructed was transfected into E. coli FERM P-22104 by the calcium chloride method (refer to Genetic Engineering Laboratory Notebook (Part I), by Takaaki Tamura, Yodosha). High expression of inositol monophosphatase was confirmed in the soluble fraction of this E. coli by SDS-PAGE.

2-b) Construction of a Plasmid for Transformation

The pNFP-D78 produced in Example 1 was digested by Sal I, blunted, and the 5' end dephosphorylated. The suhB expression cassette was cloned in pNFP-A54 and ligated into pNFP-D78. pNFP-G22 having an INO1 expression cassette and an suhB expression cassette in the forward direction ligated in pNFP-D78 was obtained. Next, pNFP-G22 was digested by Sal I, blunted, and the 5' end dephosphorylated. The iolG expression cassette in pNFP-J22 and the iolW expression cassette in pNFP-J36 were cloned, and the two expression cassettes were ligated into pNFP-G22. A plasmid having an INO1 expression cassette and suhB expression cassette and an iolG expression cassette and iolW expression cassette in the forward direction ligated in pNFP-G22 was obtained.

2-c) Scyllo-Inositol Production by Transformants Transfected by an Expression Cassette-Containing Plasmid A plasmid constructed according to the procedure described above was transfected into E. coli AKC-016 (deposited as FERM P-22104 on Apr. 20, 2011 at the Incorporated Administrative Agency National Institute of Technology and Evaluation, Patent Microorganisms Depositary. International Accession No.: FERM BP-11512) by the calcium chloride method (refer to Genetic Engineering Laboratory Notebook (Part I), by Takaaki Tamura, Yodosha).

The transformant obtained was cultured for one day at 37° C. on LB plates containing ampicillin (100 mg/L) to form colonies. Two milliliters of LB medium containing ampicillin (100 mg/L) was placed in a 15 mL test tube and inoculated by a platinum loop with colonies from the above plate. Culture was carried out at 37° C. for 3-5 hours at 180 rpm until OD (600 nm) reached approximately 0.5. This was taken as preculture broth for the main culture.

2 g/L of glucose and 30 mL of synthetic medium containing 100 mg/L of ampicillin (Table 1) were placed in a 150 mL flask; 0.6 mL of preculture broth was added, and the main culture (scyllo-inositol production test) was conducted. The culture conditions were as follows: Culture temperature 32° C.; stirring 180 rpm; culture time 16.5 h.

TABLE 1

| Synthetic medium composition | |
|---|---|
| $KH_2PO_4$ | 13.3 g |
| $(NH_4)_2HPO_4$ | 4 g |
| $MgSO_4 \cdot 7H_2O$ | 1.2 g |
| $EDTA \cdot 2Na$ | 8.4 mg |
| $CoCl_2 \cdot 6H_2O$ | 2.5 mg |
| $MnCl_2 \cdot 4H_2O$ | 15 mg |
| $CuCl_2 \cdot 2H_2O$ | 1.5 mg |
| $H_3BO_3$ | 3 mg |
| $Na_2MoO_4 \cdot 2H_2O$ | 2.5 mg |
| $Zn(CH_3COO)_2 \cdot 2H_2O$ | 13 mg |
| $FeCl_3 \cdot 6H_2O$ | 100 mg |
| total | 1 L | pH adjusted to 6.7 using 8N KOH

The above culture broth was centrifuged at 4° C. for 10 min at 10,000×g, and the supernatant was collected. The scyllo-inositol concentration in the culture supernatant was measured. Specifically, the scyllo-inositol concentration in the culture supernatant was assayed by HPLC (detector: RI, column temperature: 70° C., flow rate: 1 mL/min,) linked to KS-G (guard column), Sugar KS-801, and Sugar KS-802 (all trade names, manufactured by Showa Denko K.K.). The results of assay clarified that 0.09 g/L of scyllo-inositol was produced in the culture supernatant and that the glucose was completely consumed. On the other hand, no scyllo-inositol peak was detected in the culture supernatant in a line having unenhanced inositol monophosphatase activity at a culture time of 16.5 hours under these scyllo-inositol production conditions by synthetic medium.

Therefore, enhancement of the inositol monophosphatase activity in transformed microorganisms of the present invention was proved to be advantageous.

2-d) Scyllo-Inositol Production by Transformants Transfected by an Expression Cassette-Containing Plasmid Using a Jar Fermenter The transformant in 2-c) above was cultured for one day at 37° C. on LB plates containing ampicillin (100 mg/L) to form colonies. Thirty milliliters of LB medium containing ampicillin (100 mg/L) was placed in a 150 mL flask and inoculated by a platinum loop with colonies from the above plate. Culture was carried out at 37° C. for 3-5 hours at 180 rpm until OD (600 nm) reached approximately 0.5. This was taken as preculture broth for the main culture.

1 g/L of glucose and 300 mL of the following synthetic medium containing 100 mg/L of ampicillin (Table 2) were placed in a 1000 mL jar fermenter (manufactured by Marubishi Bioengineering); 6 mL of preculture broth was added, and the main culture (scyllo-inositol production test using a jar fermenter) was conducted. The culture conditions were as follows: Culture temperature 32° C.; culture pH 6.0 (lower limit); alkali added 28% (W/V) ammonia water; stirring at 850 rpm; ventilation 1 vvm. The glucose feed solution (Table 3) that served as the raw material was added as appropriate to adjust a glucose concentration to 0-5 g/L in the culture broth.

TABLE 6

| Synthetic medium composition | |
|---|---|
| $KH_2PO_4$ | 13.3 g |
| $(NH_4)_2HPO_4$ | 4 g |
| $MgSO_4 \cdot 7H_2O$ | 1.2 g |
| $EDTA \cdot 2Na$ | 8.4 mg |
| $CoCl_2 \cdot 6H_2O$ | 2.5 mg |
| $MnCl_2 \cdot 4H_2O$ | 15 mg |
| $CuCl_2 \cdot 2H_2O$ | 1.5 mg |
| $H_3BO_3$ | 3 mg |
| $Na_2MoO_4 \cdot 2H_2O$ | 2.5 mg |
| $Zn(CH_3COO)_2 \cdot 2H_2O$ | 13 mg |
| $FeCl_3 \cdot 6H_2O$ | 100 mg |
| total | 1 L | pH adjusted to 6.3 using 8N KOH

TABLE 7

| Glucose feed solution | |
|---|---|
| Glucose | 700 g |
| $MgSO_4 \cdot 7H_2O$ | 20 g |
| $EDTA \cdot 2Na$ | 13 mg |
| $CoCl_2 \cdot 6H_2O$ | 5 mg |
| $MnCl_2 \cdot 4H_2O$ | 29 mg |
| $CuCl_2 \cdot 2H_2O$ | 4 mg |
| $H_3BO_3$ | 5 mg |
| $Na_2MoO_4 \cdot 2H_2O$ | 4 mg |
| $Zn(CH_3COO)_2 \cdot 2H_2O$ | 21 mg |
| $FeCl_3 \cdot 6H_2O$ | 41 mg |
| total | 1 L |

After a culture time of 68 hours, the above culture broth was centrifuged at 4° C. for 10 min at 10,000×g, and the supernatant was collected. The scyllo-inositol concentration in the culture supernatant was measured. Specifically, the scyllo-inositol concentration in the culture supernatant was assayed by HPLC (detector: RI, column temperature: 70° C., flow rate: 1 mL/min,) linked to KS-G (guard column), Sugar KS-801, and Sugar KS-802 (all trade names, manufactured by Showa Denko K.K.).

As a result of assay, an unprecedented scyllo-inositol concentration of 12.4 g/L was produced in the culture supernatant. On the other hand, virtually no myo-inositol which poses a problem in the refining step was present in the culture supernatant; its concentration was 0.1% or less.

Example 3

Isolation and Determination of Structure of the Scyllo-Inositol Derivative

When the culture supernatant obtained in the scyllo-inositol production test using a jar fermenter in Example 2 was analyzed by HPLC (column: Shodex Asahipak NH₂P-50 4E (trade name, manufactured by Showa Denko K.K.; mobile phase: water/acetonitrile=25/75; flow rate: 0.8 mL/min, column temperature: 40° C.; detection: RI), 1.4 g/L of scyllo-inositol derivative was produced together with 12.4 g/L of scyllo-inositol in the culture supernatant. The peak of this scyllo-inositol derivative was collected and used in the following studies.

The structure of the compound separated was determined by NMR analysis as follows.

Instrument: Avance 600 (manufactured by Bruker Bios-pin)

Probe: Cryoprobe ($^{13}C$ high sensitivity)

Measurement temperature: 18° C. (all set at 291K (18° C.) to prevent deterioration of the sample and to move the water signal during $^1H$-NMR.)

Solvent: D$_2$O (manufactured by Aldrich)
Internal standard: TSP
$^1$H frequency: 600.13 MHz
$^{13}$C frequency: 150.92 MHz The results of measurement and assignment of peaks were as follows. Furthermore, the peak number "GH-1" in the table shows the position 1 hydrogen of the glucose residue. "IH-1" shows the position 1 hydrogen of the scyllo-inositol residue. The others are also the same.

[Chemical Formula 14]

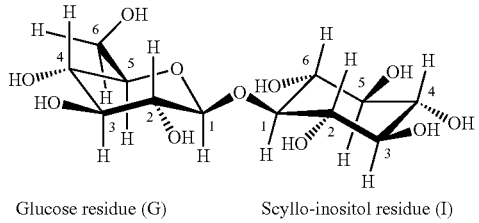

Glucose residue (G)   Scyllo-inositol residue (I)

TABLE 4

$^1$H-NMR

| Peak no. | δ H (ppm) | Peak splitting pattern | J (Hz) |
|---|---|---|---|
| GH-1 | 4.75 | d | 7.9 |
| GH-2 | 3.35-3.39 | dd | 7.9, 9.3 |
| GH-3 | 3.53 | dd | 9.3, 9.3 |
| GH-4 | 3.41 | dd | 9.4, 9.4 |
| GH-5 | 3.48 | m | 9.4, 1.9, 6.0 |
| GH-6 | 3.92 | dd | 1.9, 12.5 |
| GH-6' | 3.73 | dd | 12.5, 6.0 |
| IH-1 | 3.62 | dd | 9.3, 9.3 |
| IH-2 | 3.56 | dd | — |
| IH-3 | 3.35-3.39 | — | — |
| IH-4 | 3.35-3.39 | — | — |
| IH-5 | 3.35-3.39 | — | — |
| IH-6 | 3.45 | dd | 9.1, 9.1 |

TABLE 5

$^{13}$C-NMR

| Peak no. | δ C (ppm) |
|---|---|
| GC-1 | 105.74 |
| GC-2 | 76.35 |
| GC-3 | 78.43 |
| GC-4 | 72.40 |
| GC-5 | 78.89 |
| GC-6 | 63.51 |
| IC-1 | 84.92 |
| IC-2 | 76.30 |
| IC-3 | 76.09 |

TABLE 5-continued $^{13}$C-NMR

| Peak no. | δ C (ppm) |
|---|---|
| IC-4 | 76.17 |
| IC-5 | 76.17 |
| IC-6 | 74.86 |

Figure 6:
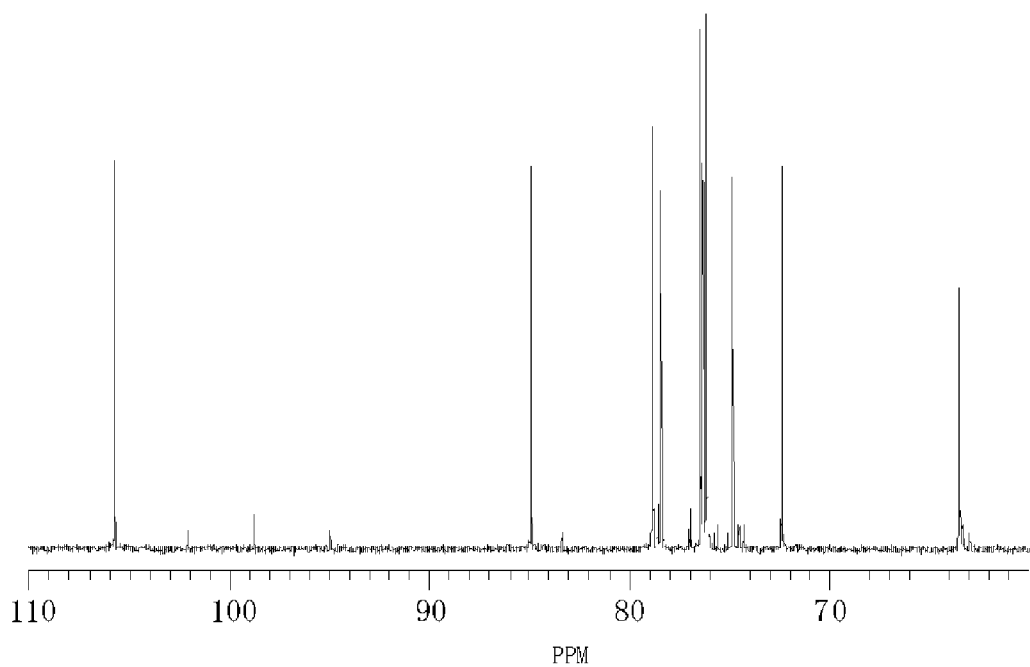
FIG. 6 is a $^{13}$C-NMR spectrum of the scyllo-inositol derivative of the present invention.

The above $^1$H-NMR and $^{13}$C-NMR are shown in FIGS. 5 and 6, respectively. The assignment of peaks was also confirmed by COSY, CH—COSY, HMBC, and J-resolved two-dimensional NMR.

Example 4

Enzymatic Decomposition of the Scyllo-Inositol Derivative

The compound obtained in Example 3 was decomposed by Cellobiase (Sigma), which is a β-glucosidase derived from mold of the genus *Aspergillus*. Specifically, the compound obtained in Example 3 was dissolved in a concentration of 6 mg/mL in 400 μL of 150 mM Bis-Tris buffer (pH=7.0). One hundred microliters of 25 U/mL Cellobiase was added to the solution and reacted by incubating (1200 rpm, Bioshaker M•BRO22, Taitec) up to 20 hours at 40° C. The reaction solution was sampled in hours 0, 3, and 20 of the reaction, and the reaction status was confirmed by HPLC (column: Shodex Asahipak NH$_2$P-50 4E (trade name: manufactured by Showa Denko K.K.), mobile phase: water/acetonitrile=25/75, flow rate: 0.8 mL/min, column temperature: 40° C., detector: RI).

Figure 7:
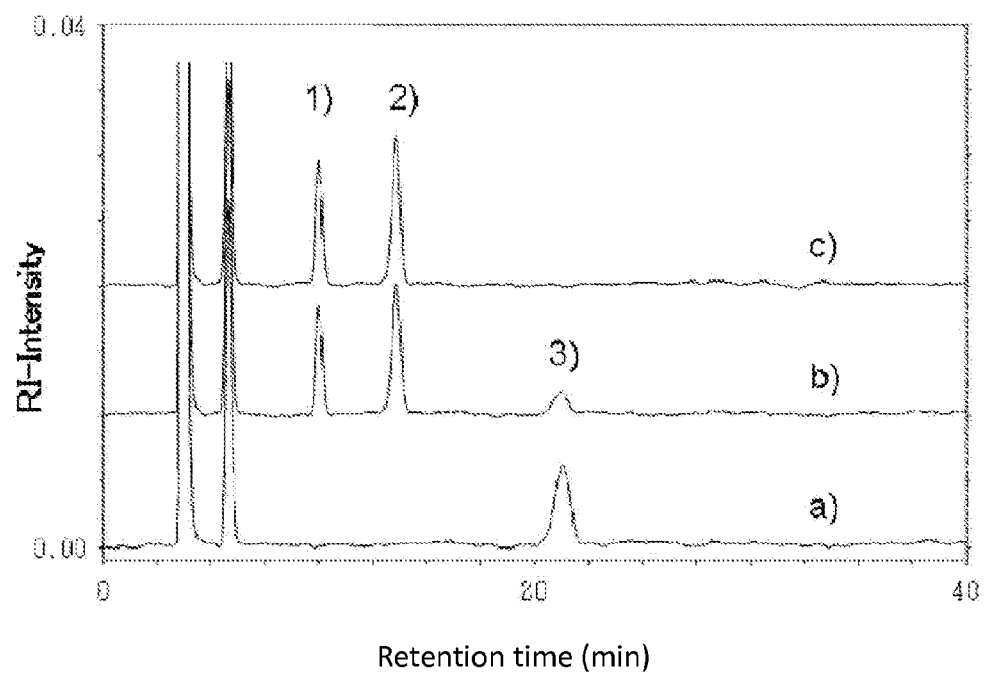
FIG. 7 is an example of decomposition of the scyllo-inositol derivative of the present invention by β-glucosidase (cellobiase).

As shown by the results in FIG. 7, virtually all of the compound obtained in Example 3, that is, the scyllo-inositol derivative of the present invention, decomposed from the start of the reaction to hour 3, and corresponding amounts of glucose and scyllo-inositol were produced. The scyllo-inositol derivative of the present invention decomposed completely from the start of the reaction to after 20 hours. The results proved that the scyllo-inositol derivative of the present invention is easily decomposed by β-glucosidase. This enzyme experiment also confirmed the correctness of the structure determined for the scyllo-inositol derivative of the present invention.

INDUSTRIAL APPLICABILITY

The present invention can be utilized in the industrial fermentative production of scyllo-inositol. The novel scyllo-inositol derivative of the present invention is also useful in the industrial production of scyllo-inositol.

When it is stated that the plasmids and microorganisms mentioned in this specification have been deposited, all were deposited with the (name of depository institution) "IPOD National Institute of Technology and Evaluation, Patent Microorganisms Depositary (IPOD, NITE)"; (address of depository institution) Central 6, 1-1 Higashi 1-chome, Tsukuba-shi, Ibaraki-ken, 305-8566."

The invention claimed is:

1. A method for producing scyllo-inositol and a scyllo-inositol derivative comprising:
preparing a transformed microorganism by transfecting a host microorganism with expression cassettes comprising an inositol-1-phosphoric acid synthase gene, inositol monophosphatase gene, myo-inositol dehydrogenase gene, and iolW gene to overexpress said genes in the transformed microorganism, wherein the host microorganism is *Escherichia coli*; and
contacting the transformed microorganism with glucose or disaccharides or polysaccharides having glucose units under conditions suited to the growth and/or maintenance of the transformed microorganism.

2. The production method according to claim 1 wherein the scyllo-inositol derivative is a compound shown by the following structural formula:

[Chemical Formula 1]

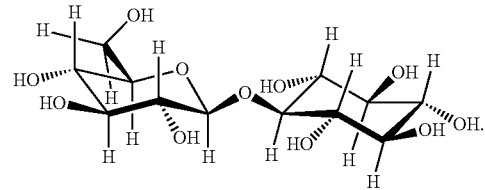

3. The method according to claim 1, wherein said expression cassettes comprises first, second, third and fourth expression cassettes comprising said inositol-1-phosphoric acid synthase gene, said inositol monophosphatase gene, said myo-inositol dehydrogenase gene, and said iolW gene, respectively.

4. The method according to claim 1, wherein said inositol monophosphatase gene is a suhB gene.

5. The method according to claim 1, wherein said inositol-1-phosphoric acid synthase gene is a INO1 gene.

* * * * *

SEQUENCE LISTING

<160> NUMBER OF SEQ ID NOS: 18

<210> SEQ ID NO 1
<211> LENGTH: 1602
<212> TYPE: DNA
<213> ORGANISM: Saccharomyces cerevisiae
<220> FEATURE:
<221> NAME/KEY: CDS
<222> LOCATION: (1)..(1602)

```
<400> SEQUENCE: 1 atg aca gaa gat aat att gct cca atc acc tcc gtt aaa gta gtt acc        48
Met Thr Glu Asp Asn Ile Ala Pro Ile Thr Ser Val Lys Val Val Thr
1               5                   10                  15 gac aag tgc acg tac aag gac aac gag ctg ctc acc aag tac agc tac        96
Asp Lys Cys Thr Tyr Lys Asp Asn Glu Leu Leu Thr Lys Tyr Ser Tyr
            20                  25                  30 gaa aat gct gta gtt acg aag aca gct agt ggc cgc ttc gat gtc acg       144
Glu Asn Ala Val Val Thr Lys Thr Ala Ser Gly Arg Phe Asp Val Thr
        35                  40                  45 ccc act gtt caa gac tac gtg ttc aaa ctt gac tta aaa aag ccg gaa       192
Pro Thr Val Gln Asp Tyr Val Phe Lys Leu Asp Leu Lys Lys Pro Glu
    50                  55                  60 aaa cta gga att atg ctc att ggg tta ggt ggc aac aat ggc tcc acc       240
Lys Leu Gly Ile Met Leu Ile Gly Leu Gly Gly Asn Asn Gly Ser Thr
65                  70                  75                  80 tta gtg gcc tcg gta ttg gcg aat aag cac aat gtg gag ttt caa act       288
Leu Val Ala Ser Val Leu Ala Asn Lys His Asn Val Glu Phe Gln Thr
                85                  90                  95 aag gaa ggc gtt aag caa cca aac tac ttc ggc tcc atg act caa tgt       336
Lys Glu Gly Val Lys Gln Pro Asn Tyr Phe Gly Ser Met Thr Gln Cys
            100                 105                 110 tct acc ttg aaa ctg ggt gtc gat gcg gag ggg aat gac gtt tat gct       384
Ser Thr Leu Lys Leu Gly Val Asp Ala Glu Gly Asn Asp Val Tyr Ala
        115                 120                 125 cct ttt aac tct ctg ttg ccc atg gtt agc cca aac gac ttt gtc gtc       432
Pro Phe Asn Ser Leu Leu Pro Met Val Ser Pro Asn Asp Phe Val Val
    130                 135                 140 tct ggt tgg gac atc aat aac gca gat cta tac gaa gct atg cag aga       480
Ser Gly Trp Asp Ile Asn Asn Ala Asp Leu Tyr Glu Ala Met Gln Arg
145                 150                 155                 160 agt cag gtt ctc gaa tat gat ctg caa caa cgc ttg aag gcg aag atg       528
Ser Gln Val Leu Glu Tyr Asp Leu Gln Gln Arg Leu Lys Ala Lys Met
                165                 170                 175 tcc ttg gtg aag cct ctt cct tcc att tac tac cct gat ttc att gca       576
Ser Leu Val Lys Pro Leu Pro Ser Ile Tyr Tyr Pro Asp Phe Ile Ala
            180                 185                 190 gct aat caa gat gag aga gcc aat aac tgc atc aat ttg gat gaa aaa       624
Ala Asn Gln Asp Glu Arg Ala Asn Asn Cys Ile Asn Leu Asp Glu Lys
        195                 200                 205 ggc aac gta acc acg agg ggt aag tgg gcc cat ctg caa cgc atc aga       672
Gly Asn Val Thr Thr Arg Gly Lys Trp Ala His Leu Gln Arg Ile Arg
    210                 215                 220 cgc gat att cag aat ttc aaa gaa gaa aac gcc ctt gat aaa gta atc       720
Arg Asp Ile Gln Asn Phe Lys Glu Glu Asn Ala Leu Asp Lys Val Ile
225                 230                 235                 240 gtt ctt tgg act gca aat act gag agg tac gta gaa gta tct cct ggt       768
Val Leu Trp Thr Ala Asn Thr Glu Arg Tyr Val Glu Val Ser Pro Gly
                245                 250                 255 gtt aat gac acc atg gaa aac ctc ttg cag tct att aag aat gac cat       816
Val Asn Asp Thr Met Glu Asn Leu Leu Gln Ser Ile Lys Asn Asp His
            260                 265                 270 gaa gag att gct cct tcc acg atc ttt gca gca gca tct atc ttg gaa       864
Glu Glu Ile Ala Pro Ser Thr Ile Phe Ala Ala Ala Ser Ile Leu Glu
        275                 280                 285 ggt gtc ccc tat att aat ggt tca ccg cag aat act ttt gtt ccc ggc       912
Gly Val Pro Tyr Ile Asn Gly Ser Pro Gln Asn Thr Phe Val Pro Gly
    290                 295                 300 ttg gtt cag ctg gct gag cat gag ggt aca ttc att gcg gga gac gat       960
```

```
Leu Val Gln Leu Ala Glu His Glu Gly Thr Phe Ile Ala Gly Asp Asp
305                 310                 315                 320 ctc aag tcg gga caa acc aag ttg aag tct gtt ctg gcc cag ttc tta      1008
Leu Lys Ser Gly Gln Thr Lys Leu Lys Ser Val Leu Ala Gln Phe Leu
                325                 330                 335 gtg gat gca ggt att aaa ccg gtc tcc att gca tcc tat aac cat tta      1056
Val Asp Ala Gly Ile Lys Pro Val Ser Ile Ala Ser Tyr Asn His Leu
            340                 345                 350 ggc aat aat gac ggt tat aac tta tct gct cca aaa caa ttt agg tct      1104
Gly Asn Asn Asp Gly Tyr Asn Leu Ser Ala Pro Lys Gln Phe Arg Ser
        355                 360                 365 aag gag att tcc aaa agt tct gtc ata gat gac atc atc gcg tct aat      1152
Lys Glu Ile Ser Lys Ser Ser Val Ile Asp Asp Ile Ile Ala Ser Asn
    370                 375                 380 gat atc ttg tac aat gat aaa ctg ggt aaa aaa gtt gac cac tgc att      1200
Asp Ile Leu Tyr Asn Asp Lys Leu Gly Lys Lys Val Asp His Cys Ile
385                 390                 395                 400 gtc att aaa tat atg aag ccc gtc ggg gac tca aaa gtg gca atg gac      1248
Val Ile Lys Tyr Met Lys Pro Val Gly Asp Ser Lys Val Ala Met Asp
                405                 410                 415 gag tat tac agt gag ttg atg tta ggt ggc cat aac cgg att tcc att      1296
Glu Tyr Tyr Ser Glu Leu Met Leu Gly Gly His Asn Arg Ile Ser Ile
            420                 425                 430 cac aat gtt tgc gaa gat tct tta ctg gct acg ccc ttg atc atc gat      1344
His Asn Val Cys Glu Asp Ser Leu Leu Ala Thr Pro Leu Ile Ile Asp
        435                 440                 445 ctt tta gtc atg act gag ttt tgt aca aga gtg tcc tat aag aag gtg      1392
Leu Leu Val Met Thr Glu Phe Cys Thr Arg Val Ser Tyr Lys Lys Val
    450                 455                 460 gac cca gtt aaa gaa gat gct ggc aaa ttt gag aac ttt tat cca gtt      1440
Asp Pro Val Lys Glu Asp Ala Gly Lys Phe Glu Asn Phe Tyr Pro Val
465                 470                 475                 480 tta acc ttc ttg agt tac tgg tta aaa gct cca tta aca aga cca gga      1488
Leu Thr Phe Leu Ser Tyr Trp Leu Lys Ala Pro Leu Thr Arg Pro Gly
                485                 490                 495 ttt cac ccg gtg aat ggc tta aac aag caa aga acc gcc tta gaa aat      1536
Phe His Pro Val Asn Gly Leu Asn Lys Gln Arg Thr Ala Leu Glu Asn
            500                 505                 510 ttt tta aga ttg ttg att gga ttg cct tct caa aac gaa cta aga ttc      1584
Phe Leu Arg Leu Leu Ile Gly Leu Pro Ser Gln Asn Glu Leu Arg Phe
        515                 520                 525 gaa gag aga ttg ttg taa                                              1602
Glu Glu Arg Leu Leu
    530

<210> SEQ ID NO 2
<211> LENGTH: 533
<212> TYPE: PRT
<213> ORGANISM: Saccharomyces cerevisiae

<400> SEQUENCE: 2

Met Thr Glu Asp Asn Ile Ala Pro Ile Thr Ser Val Lys Val Thr
1               5                   10                  15

Asp Lys Cys Thr Tyr Lys Asp Asn Glu Leu Leu Thr Lys Tyr Ser Tyr
                20                  25                  30

Glu Asn Ala Val Val Thr Lys Thr Ala Ser Gly Arg Phe Asp Val Thr
            35                  40                  45

Pro Thr Val Gln Asp Tyr Val Phe Lys Leu Asp Leu Lys Lys Pro Glu
        50                  55                  60
```

-continued

```
Lys Leu Gly Ile Met Leu Ile Gly Leu Gly Asn Asn Gly Ser Thr
 65                  70                  75                  80

Leu Val Ala Ser Val Leu Ala Asn Lys His Asn Val Glu Phe Gln Thr
                 85                  90                  95

Lys Glu Gly Val Lys Gln Pro Asn Tyr Phe Gly Ser Met Thr Gln Cys
            100                 105                 110

Ser Thr Leu Lys Leu Gly Val Asp Ala Glu Gly Asn Asp Val Tyr Ala
            115                 120                 125

Pro Phe Asn Ser Leu Leu Pro Met Val Ser Pro Asn Asp Phe Val Val
        130                 135                 140

Ser Gly Trp Asp Ile Asn Asn Ala Asp Leu Tyr Glu Ala Met Gln Arg
145                 150                 155                 160

Ser Gln Val Leu Glu Tyr Asp Leu Gln Gln Arg Leu Lys Ala Lys Met
                165                 170                 175

Ser Leu Val Lys Pro Leu Pro Ser Ile Tyr Tyr Pro Asp Phe Ile Ala
            180                 185                 190

Ala Asn Gln Asp Glu Arg Ala Asn Asn Cys Ile Asn Leu Asp Glu Lys
            195                 200                 205

Gly Asn Val Thr Thr Arg Gly Lys Trp Ala His Leu Gln Arg Ile Arg
        210                 215                 220

Arg Asp Ile Gln Asn Phe Lys Glu Glu Asn Ala Leu Asp Lys Val Ile
225                 230                 235                 240

Val Leu Trp Thr Ala Asn Thr Glu Arg Tyr Val Glu Val Ser Pro Gly
                245                 250                 255

Val Asn Asp Thr Met Glu Asn Leu Leu Gln Ser Ile Lys Asn Asp His
            260                 265                 270

Glu Glu Ile Ala Pro Ser Thr Ile Phe Ala Ala Ser Ile Leu Glu
            275                 280                 285

Gly Val Pro Tyr Ile Asn Gly Ser Pro Gln Asn Thr Phe Val Pro Gly
        290                 295                 300

Leu Val Gln Leu Ala Glu His Glu Gly Thr Phe Ile Ala Gly Asp Asp
305                 310                 315                 320

Leu Lys Ser Gly Gln Thr Lys Leu Lys Ser Val Leu Ala Gln Phe Leu
                325                 330                 335

Val Asp Ala Gly Ile Lys Pro Val Ser Ile Ala Ser Tyr Asn His Leu
            340                 345                 350

Gly Asn Asn Asp Gly Tyr Asn Leu Ser Ala Pro Lys Gln Phe Arg Ser
        355                 360                 365

Lys Glu Ile Ser Lys Ser Val Ile Asp Ile Ile Ala Ser Asn
370                 375                 380

Asp Ile Leu Tyr Asn Asp Lys Leu Gly Lys Val Asp His Cys Ile
385                 390                 395                 400

Val Ile Lys Tyr Met Lys Pro Val Gly Asp Ser Lys Val Ala Met Asp
                405                 410                 415

Glu Tyr Tyr Ser Glu Leu Met Leu Gly Gly His Asn Arg Ile Ser Ile
            420                 425                 430

His Asn Val Cys Glu Asp Ser Leu Leu Ala Thr Pro Leu Ile Ile Asp
        435                 440                 445

Leu Leu Val Met Thr Glu Phe Cys Thr Arg Val Ser Tyr Lys Lys Val
        450                 455                 460

Asp Pro Val Lys Glu Asp Ala Gly Lys Phe Glu Asn Phe Tyr Pro Val
465                 470                 475                 480

Leu Thr Phe Leu Ser Tyr Trp Leu Lys Ala Pro Leu Thr Arg Pro Gly
```

```
                485                 490                 495
Phe His Pro Val Asn Gly Leu Asn Lys Gln Arg Thr Ala Leu Glu Asn
            500                 505                 510

Phe Leu Arg Leu Leu Ile Gly Leu Pro Ser Gln Asn Glu Leu Arg Phe
            515                 520                 525

Glu Glu Arg Leu Leu
    530

<210> SEQ ID NO 3
<211> LENGTH: 804
<212> TYPE: DNA
<213> ORGANISM: Escherichia coli
<220> FEATURE:
<221> NAME/KEY: CDS
<222> LOCATION: (1)..(804)

<400> SEQUENCE: 3 atg cat ccg atg ctg aac atc gcc gtg cgc gca gcg cgc aag gcg ggt        48
Met His Pro Met Leu Asn Ile Ala Val Arg Ala Ala Arg Lys Ala Gly
1               5                   10                  15 aat tta att gcc aaa aac tat gaa acc ccg gac gct gta gaa gcg agc        96
Asn Leu Ile Ala Lys Asn Tyr Glu Thr Pro Asp Ala Val Glu Ala Ser
                20                  25                  30 cag aaa ggc agt aac gat ttc gtg acc aac gta gat aaa gct gcc gaa       144
Gln Lys Gly Ser Asn Asp Phe Val Thr Asn Val Asp Lys Ala Ala Glu
            35                  40                  45 gcg gtg att atc gac acg att cgt aaa tct tac cca cag cac acc atc       192
Ala Val Ile Ile Asp Thr Ile Arg Lys Ser Tyr Pro Gln His Thr Ile
        50                  55                  60 atc acc gaa gaa agc ggt gaa ctt gaa ggt act gat cag gat gtt caa       240
Ile Thr Glu Glu Ser Gly Glu Leu Glu Gly Thr Asp Gln Asp Val Gln
65                  70                  75                  80 tgg gtt atc gat cca ctg gat ggc act acc aac ttt atc aaa cgt ctg       288
Trp Val Ile Asp Pro Leu Asp Gly Thr Thr Asn Phe Ile Lys Arg Leu
                85                  90                  95 ccg cac ttc gcg gta tct atc gct gtt cgt atc aaa ggc cgc acc gaa       336
Pro His Phe Ala Val Ser Ile Ala Val Arg Ile Lys Gly Arg Thr Glu
                100                 105                 110 gtt gct gtg gta tac gat cct atg cgt aac gaa ctg ttc acc gcc act       384
Val Ala Val Val Tyr Asp Pro Met Arg Asn Glu Leu Phe Thr Ala Thr
            115                 120                 125 cgc ggt cag ggc gca cag ctg aac ggc tac cga ctg cgc ggc agc acc       432
Arg Gly Gln Gly Ala Gln Leu Asn Gly Tyr Arg Leu Arg Gly Ser Thr
        130                 135                 140 gct cgc gat ctc gac ggt act att ctg gcg acc ggc ttc ccg ttc aaa       480
Ala Arg Asp Leu Asp Gly Thr Ile Leu Ala Thr Gly Phe Pro Phe Lys
145                 150                 155                 160 gca aaa cag tac gcc act acc tac atc aac atc gtc ggc aaa ctg ttc       528
Ala Lys Gln Tyr Ala Thr Thr Tyr Ile Asn Ile Val Gly Lys Leu Phe
                165                 170                 175 aac gaa tgt gca gac ttc cgt cgt acc ggt tct gcg gcg ctg gat ctg       576
Asn Glu Cys Ala Asp Phe Arg Arg Thr Gly Ser Ala Ala Leu Asp Leu
                180                 185                 190 gct tac gtc gct gcg ggt cgt gtt gac ggt ttc ttt gaa atc ggt ctg       624
Ala Tyr Val Ala Ala Gly Arg Val Asp Gly Phe Phe Glu Ile Gly Leu
            195                 200                 205 cgc ccg tgg gac ttc gcc gca ggc gag ctg ctg gtt cgt gaa gcg ggc       672
Arg Pro Trp Asp Phe Ala Ala Gly Glu Leu Leu Val Arg Glu Ala Gly
        210                 215                 220 ggc atc gtc agc gac ttc acc ggt ggt cat aac tac atg ctg acc ggt       720
```

```
Gly Ile Val Ser Asp Phe Thr Gly Gly His Asn Tyr Met Leu Thr Gly
225                 230                 235                 240 aac atc gtt gct ggt aac ccg cgc gtt gtt aaa gcc atg ctg gcg aac    768
Asn Ile Val Ala Gly Asn Pro Arg Val Val Lys Ala Met Leu Ala Asn
                245                 250                 255 atg cgt gac gag tta agc gac gct ctg aag cgt taa                    804
Met Arg Asp Glu Leu Ser Asp Ala Leu Lys Arg
            260                 265
```

<210> SEQ ID NO 4
<211> LENGTH: 267
<212> TYPE: PRT
<213> ORGANISM: Escherichia coli

<400> SEQUENCE: 4

```
Met His Pro Met Leu Asn Ile Ala Val Arg Ala Ala Arg Lys Ala Gly
1               5                   10                  15

Asn Leu Ile Ala Lys Asn Tyr Glu Thr Pro Asp Ala Val Glu Ala Ser
            20                  25                  30

Gln Lys Gly Ser Asn Asp Phe Val Thr Asn Val Asp Lys Ala Ala Glu
        35                  40                  45

Ala Val Ile Ile Asp Thr Ile Arg Lys Ser Tyr Pro Gln His Thr Ile
    50                  55                  60

Ile Thr Glu Glu Ser Gly Glu Leu Glu Gly Thr Asp Gln Asp Val Gln
65                  70                  75                  80

Trp Val Ile Asp Pro Leu Asp Gly Thr Thr Asn Phe Ile Lys Arg Leu
                85                  90                  95

Pro His Phe Ala Val Ser Ile Ala Val Arg Ile Lys Gly Arg Thr Glu
            100                 105                 110

Val Ala Val Val Tyr Asp Pro Met Arg Asn Glu Leu Phe Thr Ala Thr
        115                 120                 125

Arg Gly Gln Gly Ala Gln Leu Asn Gly Tyr Arg Leu Arg Gly Ser Thr
    130                 135                 140

Ala Arg Asp Leu Asp Gly Thr Ile Leu Ala Thr Gly Phe Pro Phe Lys
145                 150                 155                 160

Ala Lys Gln Tyr Ala Thr Thr Tyr Ile Asn Ile Val Gly Lys Leu Phe
                165                 170                 175

Asn Glu Cys Ala Asp Phe Arg Arg Thr Gly Ser Ala Ala Leu Asp Leu
            180                 185                 190

Ala Tyr Val Ala Ala Gly Arg Val Asp Gly Phe Phe Glu Ile Gly Leu
        195                 200                 205

Arg Pro Trp Asp Phe Ala Ala Gly Glu Leu Leu Val Arg Glu Ala Gly
    210                 215                 220

Gly Ile Val Ser Asp Phe Thr Gly Gly His Asn Tyr Met Leu Thr Gly
225                 230                 235                 240

Asn Ile Val Ala Gly Asn Pro Arg Val Val Lys Ala Met Leu Ala Asn
                245                 250                 255

Met Arg Asp Glu Leu Ser Asp Ala Leu Lys Arg
            260                 265
```

<210> SEQ ID NO 5
<211> LENGTH: 1035
<212> TYPE: DNA
<213> ORGANISM: Bacillus subtilis
<220> FEATURE:
<221> NAME/KEY: CDS
<222> LOCATION: (1)..(1035)

```
<400> SEQUENCE: 5 atg agt tta cgt att ggc gta att gga act gga gca atc gga aaa gaa      48
Met Ser Leu Arg Ile Gly Val Ile Gly Thr Gly Ala Ile Gly Lys Glu
1               5                   10                  15 cat att aac cgt atc acg aac aag ctg tca ggc gcg gaa att gta gct      96
His Ile Asn Arg Ile Thr Asn Lys Leu Ser Gly Ala Glu Ile Val Ala
            20                  25                  30 gta acg gat gtt aat caa gaa gct gca caa aag gtc gtt gag caa tac     144
Val Thr Asp Val Asn Gln Glu Ala Ala Gln Lys Val Val Glu Gln Tyr
        35                  40                  45 caa tta aac gcg acg gtt tat ccg aat gat gac agc ttg ctt gca gac     192
Gln Leu Asn Ala Thr Val Tyr Pro Asn Asp Asp Ser Leu Leu Ala Asp
    50                  55                  60 gaa aat gta gac gct gtt tta gtg aca agc tgg ggg cct gcg cat gag     240
Glu Asn Val Asp Ala Val Leu Val Thr Ser Trp Gly Pro Ala His Glu
65                  70                  75                  80 tca agc gtg ctg aaa gcg att aaa gcc cag aaa tat gtg ttc tgt gaa     288
Ser Ser Val Leu Lys Ala Ile Lys Ala Gln Lys Tyr Val Phe Cys Glu
                85                  90                  95 aaa ccg ctc gcg aca acg gct gaa gga tgc atg cgc att gtc gaa gaa     336
Lys Pro Leu Ala Thr Thr Ala Glu Gly Cys Met Arg Ile Val Glu Glu
            100                 105                 110 gaa atc aaa gtg ggc aaa cgc ctt gtt caa gtc ggc ttc atg cgc cgt     384
Glu Ile Lys Val Gly Lys Arg Leu Val Gln Val Gly Phe Met Arg Arg
        115                 120                 125 tat gac agc ggt tac gta cag ctg aaa gaa gcg ctc gat aat cat gtc     432
Tyr Asp Ser Gly Tyr Val Gln Leu Lys Glu Ala Leu Asp Asn His Val
    130                 135                 140 atc ggc gag cct ctt atg att cac tgc gcg cac cgc aac ccg act gta     480
Ile Gly Glu Pro Leu Met Ile His Cys Ala His Arg Asn Pro Thr Val
145                 150                 155                 160 gga gat aac tat aca acg gat atg gct gta gtc gac acg ctt gtt cat     528
Gly Asp Asn Tyr Thr Thr Asp Met Ala Val Val Asp Thr Leu Val His
                165                 170                 175 gaa att gac gtg ctc cac tgg ctc gtc aat gat gac tac gag tcc gtt     576
Glu Ile Asp Val Leu His Trp Leu Val Asn Asp Asp Tyr Glu Ser Val
            180                 185                 190 caa gtc atc tat ccg aaa aaa tca aaa aac gcg ctt cca cat tta aaa     624
Gln Val Ile Tyr Pro Lys Lys Ser Lys Asn Ala Leu Pro His Leu Lys
        195                 200                 205 gat ccg caa atc gtc gtg att gaa aca aaa ggc ggt atc gtc atc aat     672
Asp Pro Gln Ile Val Val Ile Glu Thr Lys Gly Gly Ile Val Ile Asn
    210                 215                 220 gct gaa atc tat gtg aac tgt aaa tac ggc tat gac att caa tgt gaa     720
Ala Glu Ile Tyr Val Asn Cys Lys Tyr Gly Tyr Asp Ile Gln Cys Glu
225                 230                 235                 240 atc gtc gga gaa gac ggc atc atc aag ctt ccc gag cca tca agc atc     768
Ile Val Gly Glu Asp Gly Ile Ile Lys Leu Pro Glu Pro Ser Ser Ile
                245                 250                 255 agc ttg aga aaa gaa ggc aga ttc agc act gat att ttg atg gat tgg     816
Ser Leu Arg Lys Glu Gly Arg Phe Ser Thr Asp Ile Leu Met Asp Trp
            260                 265                 270 cag aga cgc ttt gtc gct gcg tat gat gtg gaa atc caa gac ttt att     864
Gln Arg Arg Phe Val Ala Ala Tyr Asp Val Glu Ile Gln Asp Phe Ile
        275                 280                 285 gat tcg att caa aag aaa ggc gag gtc agc gga ccg acg gca tgg gac     912
Asp Ser Ile Gln Lys Lys Gly Glu Val Ser Gly Pro Thr Ala Trp Asp
    290                 295                 300 ggc tat att gct gct gtc acg act gac gcg tgt gta aaa gcc cag gaa     960
Gly Tyr Ile Ala Ala Val Thr Thr Asp Ala Cys Val Lys Ala Gln Glu
```

```
Gly Tyr Ile Ala Ala Val Thr Thr Asp Ala Cys Val Lys Ala Gln Glu
305                 310                 315                 320 tct gga caa aaa gaa aag gtt gaa ttg aag gaa aaa ccg gaa ttc tat    1008
Ser Gly Gln Lys Glu Lys Val Glu Leu Lys Glu Lys Pro Glu Phe Tyr
                325                 330                 335 caa tct ttt aca aca gtt caa aac taa                                1035
Gln Ser Phe Thr Thr Val Gln Asn
            340
```

<210> SEQ ID NO 6
<211> LENGTH: 344
<212> TYPE: PRT
<213> ORGANISM: Bacillus subtilis

<400> SEQUENCE: 6

```
Met Ser Leu Arg Ile Gly Val Ile Gly Thr Gly Ala Ile Gly Lys Glu
1               5                   10                  15

His Ile Asn Arg Ile Thr Asn Lys Leu Ser Gly Ala Glu Ile Val Ala
                20                  25                  30

Val Thr Asp Val Asn Gln Glu Ala Ala Gln Lys Val Val Glu Gln Tyr
            35                  40                  45

Gln Leu Asn Ala Thr Val Tyr Pro Asn Asp Asp Ser Leu Leu Ala Asp
    50                  55                  60

Glu Asn Val Asp Ala Val Leu Val Thr Ser Trp Gly Pro Ala His Glu
65                  70                  75                  80

Ser Ser Val Leu Lys Ala Ile Lys Ala Gln Lys Tyr Val Phe Cys Glu
                85                  90                  95

Lys Pro Leu Ala Thr Thr Ala Glu Gly Cys Met Arg Ile Val Glu Glu
                100                 105                 110

Glu Ile Lys Val Gly Lys Arg Leu Val Gln Val Gly Phe Met Arg Arg
            115                 120                 125

Tyr Asp Ser Gly Tyr Val Gln Leu Lys Glu Ala Leu Asp Asn His Val
130                 135                 140

Ile Gly Glu Pro Leu Met Ile His Cys Ala His Arg Asn Pro Thr Val
145                 150                 155                 160

Gly Asp Asn Tyr Thr Thr Asp Met Ala Val Val Asp Thr Leu Val His
                165                 170                 175

Glu Ile Asp Val Leu His Trp Leu Val Asn Asp Tyr Glu Ser Val
            180                 185                 190

Gln Val Ile Tyr Pro Lys Lys Ser Lys Asn Ala Leu Pro His Leu Lys
    195                 200                 205

Asp Pro Gln Ile Val Val Ile Glu Thr Lys Gly Gly Ile Val Ile Asn
210                 215                 220

Ala Glu Ile Tyr Val Asn Cys Lys Tyr Gly Tyr Asp Ile Gln Cys Glu
225                 230                 235                 240

Ile Val Gly Glu Asp Gly Ile Ile Lys Leu Pro Glu Pro Ser Ser Ile
                245                 250                 255

Ser Leu Arg Lys Glu Gly Arg Phe Ser Thr Asp Ile Leu Met Asp Trp
                260                 265                 270

Gln Arg Arg Phe Val Ala Ala Tyr Asp Val Glu Ile Gln Asp Phe Ile
            275                 280                 285

Asp Ser Ile Gln Lys Lys Gly Glu Val Ser Gly Pro Thr Ala Trp Asp
    290                 295                 300

Gly Tyr Ile Ala Ala Val Thr Thr Asp Ala Cys Val Lys Ala Gln Glu
305                 310                 315                 320
```

```
                Ser Gly Gln Lys Glu Lys Val Glu Leu Lys Glu Lys Pro Glu Phe Tyr
                            325                 330                 335

Gln Ser Phe Thr Thr Val Gln Asn
                            340

<210> SEQ ID NO 7
<211> LENGTH: 1077
<212> TYPE: DNA
<213> ORGANISM: Bacillus subtilis
<220> FEATURE:
<221> NAME/KEY: CDS
<222> LOCATION: (1)..(1077)

<400> SEQUENCE: 7 atg ata acg ctt tta aag ggg aga aga aaa gtg gat acg atc aag gtt       48
Met Ile Thr Leu Leu Lys Gly Arg Arg Lys Val Asp Thr Ile Lys Val
1               5                   10                  15 gga ata tta gga tac gga ttg tcc ggt tct gtt ttt cac ggg ccg ctg       96
Gly Ile Leu Gly Tyr Gly Leu Ser Gly Ser Val Phe His Gly Pro Leu
                20                  25                  30 ctg gat gtt ctg gat gaa tat caa atc agc aaa atc atg aca tca cgg      144
Leu Asp Val Leu Asp Glu Tyr Gln Ile Ser Lys Ile Met Thr Ser Arg
            35                  40                  45 aca gaa gaa gtg aaa cgg gat ttt cca gat gct gag gtt gta cat gag      192
Thr Glu Glu Val Lys Arg Asp Phe Pro Asp Ala Glu Val Val His Glu
        50                  55                  60 ctt gaa gaa atc aca aat gac cct gcc att gag ctt gtc att gtc acc      240
Leu Glu Glu Ile Thr Asn Asp Pro Ala Ile Glu Leu Val Ile Val Thr
65                  70                  75                  80 acc ccg agc ggc ctt cat tac gag cat act atg gca tgc ata cag gcc      288
Thr Pro Ser Gly Leu His Tyr Glu His Thr Met Ala Cys Ile Gln Ala
                85                  90                  95 gga aaa cat gtt gtg atg gaa aaa cca atg aca gca acg gcc gaa gag      336
Gly Lys His Val Val Met Glu Lys Pro Met Thr Ala Thr Ala Glu Glu
                100                 105                 110 ggg gaa aca tta aaa agg gct gcc gat gaa aaa ggc gta tta tta agc      384
Gly Glu Thr Leu Lys Arg Ala Ala Asp Glu Lys Gly Val Leu Leu Ser
            115                 120                 125 gta tat cat aac cga cgc tgg gat aac gat ttt tta acg att aaa aag      432
Val Tyr His Asn Arg Arg Trp Asp Asn Asp Phe Leu Thr Ile Lys Lys
        130                 135                 140 ctg atc tct gag gga tcc ctt gaa gat atc aat aca tat caa gtt tcc      480
Leu Ile Ser Glu Gly Ser Leu Glu Asp Ile Asn Thr Tyr Gln Val Ser
145                 150                 155                 160 tat aac cgc tac aga cct gaa gtt caa gcg cgg tgg cgg gaa aaa gaa      528
Tyr Asn Arg Tyr Arg Pro Glu Val Gln Ala Arg Trp Arg Glu Lys Glu
                165                 170                 175 ggc act gcc act ggt acg ctg tat gat ctc ggc tcc cac atc ata gac      576
Gly Thr Ala Thr Gly Thr Leu Tyr Asp Leu Gly Ser His Ile Ile Asp
                180                 185                 190 caa acc ctg cat ttg ttt ggg atg cct aaa gcc gtg act gca aac gtg      624
Gln Thr Leu His Leu Phe Gly Met Pro Lys Ala Val Thr Ala Asn Val
            195                 200                 205 atg gcc cag cgg gaa aat gcc gaa acg gtt gac tat ttt cat tta acc      672
Met Ala Gln Arg Glu Asn Ala Glu Thr Val Asp Tyr Phe His Leu Thr
        210                 215                 220 ctg gat tat ggc aag ctt caa gcc att cta tac gga gga tca atc gtt      720
Leu Asp Tyr Gly Lys Leu Gln Ala Ile Leu Tyr Gly Gly Ser Ile Val
225                 230                 235                 240 ccg gca aac gga cct cgt tat caa atc cat gga aaa gat tct agc ttt      768
Pro Ala Asn Gly Pro Arg Tyr Gln Ile His Gly Lys Asp Ser Ser Phe
```

```
                        245                 250                 255
atc aaa tat gga att gac gga cag gaa gac gca ctc aga gcg gga aga      816
Ile Lys Tyr Gly Ile Asp Gly Gln Glu Asp Ala Leu Arg Ala Gly Arg
            260                 265                 270 aaa cca gag gat gac agc tgg ggt gcg gat gtt ccg gag ttt tac gga      864
Lys Pro Glu Asp Asp Ser Trp Gly Ala Asp Val Pro Glu Phe Tyr Gly
                275                 280                 285 aag ctt aca acc att cgt ggc tcc gac aaa aaa aca gaa acg att cca      912
Lys Leu Thr Thr Ile Arg Gly Ser Asp Lys Lys Thr Glu Thr Ile Pro
        290                 295                 300 tca gta aat ggc tcc tac ctt act tat tac cgt aaa ata gcg gaa agc      960
Ser Val Asn Gly Ser Tyr Leu Thr Tyr Tyr Arg Lys Ile Ala Glu Ser
305                 310                 315                 320 ata cga gaa ggt gct gcg ctg cca gtc act gct gag gaa ggt att aat     1008
Ile Arg Glu Gly Ala Ala Leu Pro Val Thr Ala Glu Glu Gly Ile Asn
                325                 330                 335 gtc atc cgc atc att gaa gcc gcg atg gaa agc agt aaa gag aaa cga     1056
Val Ile Arg Ile Ile Glu Ala Ala Met Glu Ser Ser Lys Glu Lys Arg
            340                 345                 350 acc att atg ctg gag cac taa                                         1077
Thr Ile Met Leu Glu His
            355
```

<210> SEQ ID NO 8
<211> LENGTH: 358
<212> TYPE: PRT
<213> ORGANISM: Bacillus subtilis

<400> SEQUENCE: 8

```
Met Ile Thr Leu Leu Lys Gly Arg Arg Lys Val Asp Thr Ile Lys Val
1               5                   10                  15

Gly Ile Leu Gly Tyr Gly Leu Ser Gly Ser Val Phe His Gly Pro Leu
            20                  25                  30

Leu Asp Val Leu Asp Glu Tyr Gln Ile Ser Lys Ile Met Thr Ser Arg
        35                  40                  45

Thr Glu Glu Val Lys Arg Asp Phe Pro Asp Ala Glu Val Val His Glu
    50                  55                  60

Leu Glu Glu Ile Thr Asn Asp Pro Ala Ile Glu Leu Val Ile Val Thr
65                  70                  75                  80

Thr Pro Ser Gly Leu His Tyr Glu His Thr Met Ala Cys Ile Gln Ala
                85                  90                  95

Gly Lys His Val Val Met Glu Lys Pro Met Thr Ala Thr Ala Glu Glu
            100                 105                 110

Gly Glu Thr Leu Lys Arg Ala Ala Asp Glu Lys Gly Val Leu Leu Ser
        115                 120                 125

Val Tyr His Asn Arg Arg Trp Asp Asn Asp Phe Leu Thr Ile Lys Lys
    130                 135                 140

Leu Ile Ser Glu Gly Ser Leu Glu Asp Ile Asn Thr Tyr Gln Val Ser
145                 150                 155                 160

Tyr Asn Arg Tyr Arg Pro Glu Val Gln Ala Arg Trp Arg Glu Lys Glu
                165                 170                 175

Gly Thr Ala Thr Gly Thr Leu Tyr Asp Leu Gly Ser His Ile Ile Asp
            180                 185                 190

Gln Thr Leu His Leu Phe Gly Met Pro Lys Ala Val Thr Ala Asn Val
        195                 200                 205

Met Ala Gln Arg Glu Asn Ala Glu Thr Val Asp Tyr Phe His Leu Thr
    210                 215                 220
```

```
Leu Asp Tyr Gly Lys Leu Gln Ala Ile Leu Tyr Gly Gly Ser Ile Val
225                 230                 235                 240

Pro Ala Asn Gly Pro Arg Tyr Gln Ile His Gly Lys Asp Ser Ser Phe
                245                 250                 255

Ile Lys Tyr Gly Ile Asp Gly Gln Glu Asp Ala Leu Arg Ala Gly Arg
            260                 265                 270

Lys Pro Glu Asp Asp Ser Trp Gly Ala Asp Val Pro Glu Phe Tyr Gly
        275                 280                 285

Lys Leu Thr Thr Ile Arg Gly Ser Asp Lys Lys Thr Glu Thr Ile Pro
    290                 295                 300

Ser Val Asn Gly Ser Tyr Leu Thr Tyr Tyr Arg Lys Ile Ala Glu Ser
305                 310                 315                 320

Ile Arg Glu Gly Ala Ala Leu Pro Val Thr Ala Glu Glu Gly Ile Asn
                325                 330                 335

Val Ile Arg Ile Ile Glu Ala Ala Met Glu Ser Ser Lys Glu Lys Arg
            340                 345                 350

Thr Ile Met Leu Glu His
        355
```

<210> SEQ ID NO 9
<211> LENGTH: 22
<212> TYPE: DNA
<213> ORGANISM: Artificial Sequence
<220> FEATURE:
<223> OTHER INFORMATION: Forward PCR Primer for INO1 Coding Region

<400> SEQUENCE: 9
atgacagaag ataatattgc tc                                           22

<210> SEQ ID NO 10
<211> LENGTH: 19
<212> TYPE: DNA
<213> ORGANISM: Artificial Sequence
<220> FEATURE:
<223> OTHER INFORMATION: Reverse PCR Primer for INO1 Coding Region

<400> SEQUENCE: 10
ttacaacaat ctctcttcg                                               19

<210> SEQ ID NO 11
<211> LENGTH: 155
<212> TYPE: DNA
<213> ORGANISM: Artificial Sequence
<220> FEATURE:
<223> OTHER INFORMATION: Promoter for INO1 coding sequence

<400> SEQUENCE: 11
ctcaagccca aaggaagagt gaggcgagtc agtcgcgtaa tgcttaggca caggattgat    60
ttgtcgcaat gattgacacg attccgcttg acgctgcgta aggttttgt aattttacag    120 gcaacctttt attcactaac aaatagctgg tggaa                             155

<210> SEQ ID NO 12
<211> LENGTH: 22
<212> TYPE: DNA
<213> ORGANISM: Artificial Sequence
<220> FEATURE:
<223> OTHER INFORMATION: Forward PCR Primer for iolG Coding Region

<400> SEQUENCE: 12
atgagtttac gtattggcgt aa                                           22

<210> SEQ ID NO 13
<211> LENGTH: 27
<212> TYPE: DNA
<213> ORGANISM: Artificial Sequence
<220> FEATURE:
<223> OTHER INFORMATION: Reverse PCR Primer for iolG Coding Region

<400> SEQUENCE: 13
ttagttttga actgttgtaa aagattg                                27

<210> SEQ ID NO 14
<211> LENGTH: 21
<212> TYPE: DNA
<213> ORGANISM: Artificial Sequence
<220> FEATURE:
<223> OTHER INFORMATION: Forward PCR Primer for iolW Coding Region

<400> SEQUENCE: 14
atgataacgc ttttaaaggg g                                      21

<210> SEQ ID NO 15
<211> LENGTH: 20
<212> TYPE: DNA
<213> ORGANISM: Artificial Sequence
<220> FEATURE:
<223> OTHER INFORMATION: Reverse PCR Primer for iolW Coding Region

<400> SEQUENCE: 15
ttagtgctcc agcataatgg                                        20

<210> SEQ ID NO 16
<211> LENGTH: 18
<212> TYPE: DNA
<213> ORGANISM: Artificial Sequence
<220> FEATURE:
<223> OTHER INFORMATION: Forward PCR Primer for suhB Coding Region

<400> SEQUENCE: 16
atgcatccga tgctgaac                                          18

<210> SEQ ID NO 17
<211> LENGTH: 19
<212> TYPE: DNA
<213> ORGANISM: Artificial Sequence
<220> FEATURE:
<223> OTHER INFORMATION: Reverse PCR Primer for suhB Coding Region

<400> SEQUENCE: 17
ttaacgcttc agagcgtcg                                         19

<210> SEQ ID NO 18
<211> LENGTH: 109
<212> TYPE: DNA
<213> ORGANISM: Artificial Sequence
<220> FEATURE:
<223> OTHER INFORMATION: Promoter for suhB coding region

<400> SEQUENCE: 18 gtcgttttc tgcttaggat tttgttattt aaattaagcc tgtaatgcct tgcttccatt    60
gcggataaat cctactttt tattgccttc aaataaattt aaggagttc              109